(12) United States Patent
Parkchoo et al.

(10) Patent No.: US 8,604,214 B2
(45) Date of Patent: Dec. 10, 2013

(54) COMPOUNDS FOR ALLEVIATION, PREVENTION OR TREATMENT OF OSTEOPOROSIS, THE PREPARATION THEREOF AND PHARMACEUTICAL COMPOSITION COMPRISING THE SAME

(75) Inventors: Hea-Young Parkchoo, Seoul (KR); Kyung-Eun Doh, Seoul (KR); Mijung Yim, Seoul (KR); Jung-Min Lee, Ansan-si (KR)

(73) Assignee: Ewha University-Industry Collaboration Foundation, Seoul (KR)

( * ) Notice: Subject to any disclaimer, the term of this patent is extended or adjusted under 35 U.S.C. 154(b) by 0 days.

(21) Appl. No.: 13/523,612

(22) Filed: Jun. 14, 2012

(65) Prior Publication Data
US 2013/0040999 A1    Feb. 14, 2013

(30) Foreign Application Priority Data
Jun. 17, 2011    (KR) ........................ 10-2011-0059302

(51) Int. Cl.
*A61K 31/428*    (2006.01)
*C07D 277/68*    (2006.01)
(52) U.S. Cl.
USPC ........................... 548/169; 548/173; 514/367

(58) Field of Classification Search
USPC ................................................ 548/169, 173
See application file for complete search history.

(56) References Cited

FOREIGN PATENT DOCUMENTS

CA        2158994 A1 *   9/1994
KR    10-2008-0099871 A   11/2008

OTHER PUBLICATIONS

Souillac, et al., Characterization of Delivery Systems, Differential Scanning Calorimetry in Encyclopedia of Controlled Drug Delivery, 1999, John Wiley & Sons, pp. 212-227.*
Vippagunta et al., Advanced Drug Delivery Reviews, 48 (2001), pp. 3-26.*

* cited by examiner

*Primary Examiner* — Laura L. Stockton
(74) *Attorney, Agent, or Firm* — Seed IP Law Group PLLC

(57) ABSTRACT

The present invention provides novel compounds of Chemical Formula I, a pharmaceutically acceptable salt thereof, or a hydrate or solvate thereof, a preparation thereof and a composition for the alleviation, prevention or treatment of osteoporosis, comprising thereof in an effective amount, and a method for alleviating, preventing or treating osteoporosis.

12 Claims, 5 Drawing Sheets

COMPOUNDS FOR ALLEVIATION, PREVENTION OR TREATMENT OF OSTEOPOROSIS, THE PREPARATION THEREOF AND PHARMACEUTICAL COMPOSITION COMPRISING THE SAME

PRIORITY STATEMENT

This application claims priority under 35 U.S.C. §119 to Korean Patent Application No. 10-2011-0059302 filed on Jun. 17, 2007 in the Korean Intellectual Property Office (KIPO), the contents of which are herein incorporated by reference in their entirety.

BACKGROUND

1. Field of the Invention

The present invention relates to novel compounds, a preparation thereof and a pharmaceutical composition comprising the same for the alleviation, prophylaxis or treatment of osteoporosis. More particularly, the present invention relates to the novel compounds inhibiting differentiation of osteoclasts, a preparation thereof and a pharmaceutical composition comprising the same for the alleviation, prophylaxis or treatment of osteoporosis.

2. Description of the Related Art

Osteoporosis is a common disease around the world, with about two hundred million persons worldwide affected thereby or suffering from low bone mass. In osteoporosis, the bone mass is reduced and the bone microarchitecture deteriorates, resulting in weakened bones. Thus, osteoporosis is a disease of the bone characterized by the increased risk of fracture particularly in the backbone, the hip joint, the carpal, the humerus, and the pelvis.

A. Bone

The three main types of cells constituting the bone are osteoblasts, osteocytes and osteoclasts. Osteoblasts are anabolic: they stimulate new bone formation by synthesizing osteoid, the organic portion of the bone matrix, which mineralizes to become bone. Osteoblasts arise from osteoprogenitor cells located in the bone marrow. The formation of osteoid completes within a relatively short period of time, typical 6~12 hours, whereas it takes a much longer time, i.e. 1~2 months, to accomplish the subsequent mineralization. After formation of the bone, osteoblasts become entrapped in the bone matrix to become osteocytes.

Osteocytes are the most numerous cells found in bone. It has been proposed that they play an integral role in the action of mechanostat, that is, in transmitting local strain information to enable the bone multicellular unit to adjust the bone content in response to the local need. Osteoclasts are large, multinucleated cells that are formed by the fusion of cells of the monocyte-macrophage cell line. Osteoclasts are catabolic: they destroy constituents of the bone through the action of lysosomal enzymes at specific sites. Pathway associated with receptor activation of nuclear factor κB ligand (RANKL) functions as a key factor in osteoclast differentiation and activation.

In addition, the RANKL/RANK/OPG system is currently regarded as the most important route for the regulation of bone resorption. RANKL is a member of the tumor necrosis factor (TNF) cytokine family, and is expressed by osteoblasts. RANKL binds to the membrane bound receptor RANK of osteoclasts to promote the differentiation of osteoclasts from hematopoetic cells. Promotion of expression of RANKL is induced by hormones such as parathyroid hormone (PTH), calcitriol and prostaglandin. Osteoclasts secret soluble receptor called osteoprotegerin (OPG). OPG is an important regulating factor as a potent antagonist in formation of osteoclasts which bind to RANKL to inactivate. OPG is stimulated by estrogen.

B. Factors for Osteoporosis

Osteoporosis is classified when the bone mineral density is 2.5 or lower or T-score (T-score is the number of standard deviations the bone mineral density measurement is above or below the young normal reference mean bone mineral density) is −2.5 or lower. Bone loss increases with age, starting in the forties or fifties. At this time, osteoporosis occurs because bone resorption by osteoclasts is increased, and bone formation by osteoblasts is decreased. In women, bone loss is accelerated by menopause. Peak bone mass is usually reached by the age of 30, acting as an important determinant for the subsequent bone mass. Peak bone mass is largely determined by the genetic makeup and is affected by other factors including nutrition, particularly the intake of calcium and vitamin D, hormone state, body exercise, smoking, low body weight, the time of adolescence, etc.

Estrogen deficiency is considered to be a decisive factor for osteoporosis, which is inferred from the highest prevalence of osteoporosis in post-menopausal women who experience natural decreases in estrogen levels. Estrogen deficiency following menopause is correlated with an increase in bone resorption, giving rise to rapid and persistent bone loss. Estrogen plays an important role in bone resorption in males as well as females, and has an effect on the achievement of peak bone mass. In addition, osteoporosis in senile males is more greatly associated with a low estrogen level than with a low androgen level.

Calcium deficiency has early been pointed out as a primary cause of osteoporosis (particularly in the elderly). Calcium deficiency, whether due to low calcium intake or hypercalcuria, increases PTH (parathyroid hormone) secretion and bone resorption. PTH, which is a peptide composed of 84 amino acids, is essential for the regulation of calcium homeostasis and its serum level is inversely correlated with calcium concentration in bone. Calcium binds to the calcium-sensing receptor in parathyroid cells to influence the release of PTH. PTH enhances renal calcium reabsorption, intestinal calcium uptake and bone remodeling. Vitamin D deficiency and secondary hyperparathyroidism are often occurred in the elderly, contributing to senile osteoporosis. Secondary hyperparathyroidism occurs when there is relative insufficiency of vitamin D, that is, where the levels of the circulating form, 25-hydroxy vitamin D, fall below 30 ng/mL, suggesting that the target for vitamin D supplementation should be at this level or higher. The active hormonal form, 1,25-dihydroxy vitamin D (calcitriol), is not only necessary for intestinal absorption of calcium and phosphorus, but also exerts a tonic inhibitory effect on PTH synthesis, so that there are dual pathways that can lead to secondary hyperparathyroidism. Vitamin D deficiency and secondary hyperparathyroidism can contribute not only to accelerated bone loss and increasing fragility, but also to neuromuscular impairment that can increase the risk of falls.

C. Design of New Therapeutics for Osteoporosis

Medicines currently used for osteoporosis include bisphosphonates agents (allendronate, etidronate, etc.), hormonal agents (raloxifene), vitamin D agents, calcitonin agents and calcium agents, etc. Commonly, the medicines for osteoporosis are not likely to elicit patient compliance and persistent medicine intake. Oral bisphosphonates can induce upper gastrointestinal side effects, so that patients must take them together with a sufficient amount of water on an empty stomach and sit upright for 30~60 minutes after the uptake of the medication, without ingesting foods or beverages. Thus, there are a lot of precaution for administration of medication. Also, there are concerns that long-term bisphosphonate use can induce excess ossification and an increase of micro-cracks in the bone by excessively inhibiting remodeling of and unable to recover the bone fracture and micro damage. Hormonal agents cause side effects as large as the therapeutic effects. PTH is required to be taken through a subcutaneous route every day and is expensive. Intake of calcium and vitamin D alone does not guarantee reliable pharmaceutical efficacy. Osteoporosis is not cured by short-term use of drugs, but its therapy requires the administration of medication over a long period of time. There is therefore the need for a novel medication that guarantees excellent pharmaceutical efficacy without engendering side effects even upon long-term use.

SUMMARY OF THE INVENTION

According to one aspect of the present invention, there is provided a novel compound represented by the following Chemical Formula I, a pharmaceutically acceptable salt thereof, or a hydrate or solvate thereof:

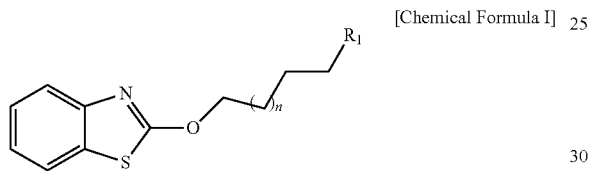

[Chemical Formula I]

wherein,
n is 1 or 2, and
$R_1$ is fluoro, chloro, bromo, iodo,

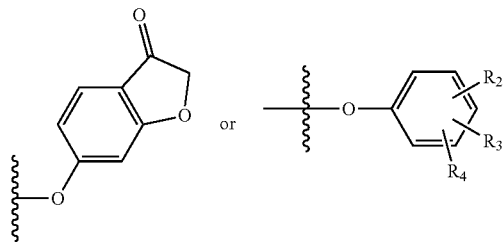

wherein $R_2$, $R_3$ and $R_4$ may be independently bonded to at least one of the carbon atoms of the phenyl ring at ortho-, meta- or para-position to the carbon atom to which the oxygen atom is attached, and is independently a hydrogen atom, fluoro, chloro, bromo, iodo, cyano, nitro, C1-4 alkyl, C1-4 alkoxy, C2-4 alkenyl, triazole, piperidine, pyridine or

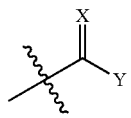

wherein X is —NOH, —NH.HCl, O or S and Y is —NR$_5$R$_6$ or —OR$_7$ wherein R$_5$, R$_6$ and R$_7$ are independently a hydrogen atom or C1-4 alkyl.

According to example embodiments of the present invention, wherein n is 1 or 2 in the compound represented by the Chemical Formula I, and $R_1$ is chloro,

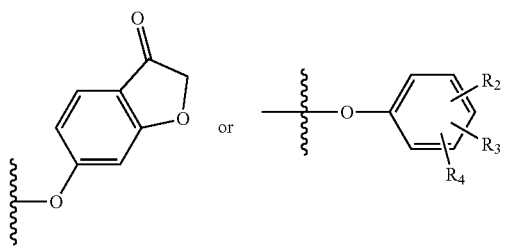

wherein $R_2$, $R_3$ and $R_4$ may be independently bonded to at least one of the carbon atoms of the phenyl ring at ortho-, meta- or para-position to the carbon atom to which the oxygen atom is attached, and is independently a hydrogen atom, fluoro, chloro, bromo, iodo, cyano, C1-4 alkyl, C1-4 alkoxy, triazole, or

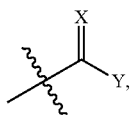

wherein X is —NOH, —NH.HCl or O and Y is NR$_5$R$_6$ or —OR$_7$, wherein R$_5$, R$_6$ and R$_7$ are independently an hydrogen atom or C1-4 alkyl.

According to example embodiments of the present invention, the compound represented by the following Chemical Formula I, a pharmaceutically acceptable salt thereof, or a hydrate or solvate thereof may include:
2-(5-chloropentyloxy)benzo[d]thiazole,
2-(5-phenoxypentyloxy)benzo[d]thiazole,
4-(5-(benzo[d]thiazol-2-yloxy)pentyloxy)benzonitrile,
4-(5-(benzo[d]thiazol-2-yloxy)pentyloxy)-N-hydroxybenzamidine,
4-(5-(benzo[d]thiazol-2-yloxy)pentyloxy)benzamidine HCl,
methyl 4-(5-(benzo[d]thiazol-2-yloxy)pentyloxy)-3-methoxybenzoate,
4-(5-(benzo[d]thiazol-2-yloxy)pentyloxy)-3-methoxybenzoic acid,
4-(5-(benzo[d]thiazol-2-yloxy)pentyloxy)-N,N-diisopropyl-3-methoxy benzamide,
4-(5-(benzo[d]thiazol-2-yloxy)pentyloxy)-N,N-diethyl-3-methoxybenzamide,
2-(5-(3,5-dimethylphenoxy)pentyloxy)benzo[d]thiazole,
2-(5-(4-(1H-1,2,4-thiazol-1-yl)phenoxy)pentyloxy)benzo[d]thiazole,
2-(5-(4-fluorophenoxy)pentyloxy)benzo[d]thiazole,
2-(5-(3-chlorophenoxy)pentyloxy)benzo[d]thiazole,
6-(5-(benzo[d]thiazol-2-yloxy)pentyloxy)benzofuran-3(2H)-one,
2-(5-(2-methoxyphenoxy)pentyloxy)benzo[d]thiazole,
2-(5-(2-fluorophenoxy)pentyloxy)benzo[d]thiazole,
2-(4-chlorobutoxy)benzo[d]thiazole,
2-(4-phenoxybutoxy)benzo[d]thiazole,
4-(4-(benzo[d]thiazol-2-yloxy)butoxy)benzonitrile,
4-(4-(benzo[d]thiazol-2-yloxy)butoxy)-N-hydroxybenzamidine,
4-(4-(benzo[d]thiazol-2-yloxy)butoxy)-N,N-diisopropyl-3-methoxybenzamide and pharmaceutically acceptable salts thereof, a hydrate or solvate thereof.

According to another aspect of the present invention, there is provided a method for preparing the compound of Chemical Formula I, comprising:

a) reacting 2-hydroxybenzothiazole with 1-bromo-5-chloropentane or 1-bromo-4-chlorobutane in the presence of a base to give a compound represented by the following Chemical Formula II; and b) reacting the compound of Chemical Formula II with a compound represented by the following Chemical Formula III in the presence of a base to synthesize the compound of Chemical Formula I:

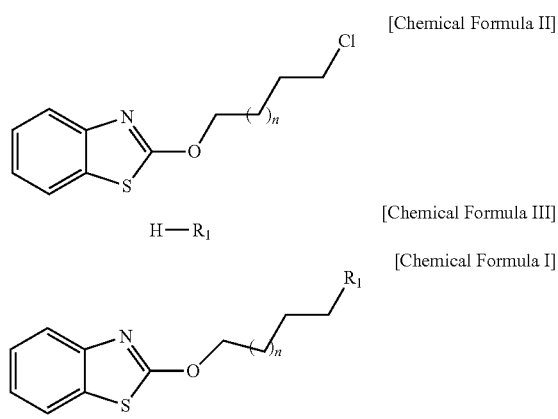

[Chemical Formula II]

[Chemical Formula III]

[Chemical Formula I]

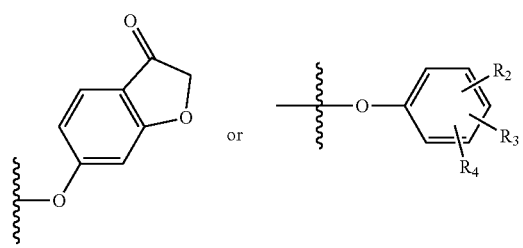

wherein,
n is 1 or 2, and
R₁ is

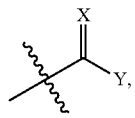

wherein R₂, R₃ and R₄ may be independently bonded to at least one of the carbon atoms of the phenyl ring at ortho-, meta- or para-position to the carbon atom to which the oxygen atom is attached, and is independently a hydrogen atom, fluoro, chloro, bromo, iodo, cyano, nitro, C1-4 alkyl, C1-4 alkoxy, C2-4 alkenyl, triazole, piperidine, pyridine or wherein X is —NOH, O or S and Y is NR₅R₆ or —OR₇, wherein R₅, R₆ and R₇ are independently an hydrogen atom or C1-4 alkyl.

According to example embodiments of the present invention, in step a) of the method of the present invention, the base may include potassium carbonate, sodium carbonate, calcium carbonate and sodium phosphate or a mixture thereof.

According to example embodiments of the present invention, in step b) of the method of the present invention, the base may include sodium hydroxide, potassium hydroxide, sodium carbonate, calcium carbonate and sodium phosphate or a mixture thereof.

According to example embodiments of the present invention, in steps a) and b) of the method of the present invention, a reaction temperature may be from about 50 to 90° C.

According to still another aspect of the present invention, there is provided a composition for the alleviation, prevention or treatment of osteoporosis, comprising a novel compound represented by the following Chemical Formula 1, a pharmaceutically acceptable salt thereof, or a hydrate or solvate thereof in an effective amount:

[Chemical Formula I]

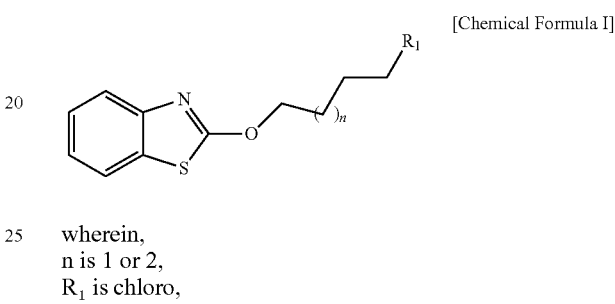

wherein,
n is 1 or 2,
R₁ is chloro,

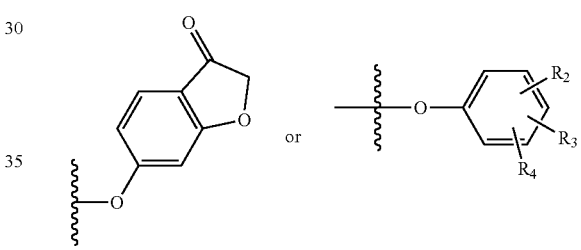

wherein R₂, R₃ and R₄ may be independently bonded to at least one of the carbon atoms of the phenyl ring at ortho-, meta- or para-position to the carbon atom to which the oxygen atom is attached, and is independently a hydrogen atom, fluoro, chloro, bromo, iodo, cyano, nitro, C1-4 alkyl, C1-4 alkoxy, C2-4 alkenyl, triazole, piperidine, pyridine or

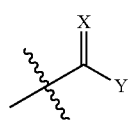

wherein X is —NOH, —NH.HCl, O or S and Y is —NR₅R₆ or —OR₇ wherein R₅, R₆ and R₇ are independently a hydrogen atom or C1-4 alkyl.

According to still another aspect of the present invention, there is provided a method for alleviating, preventing or treating osteoporosis, comprising administering the compound of Chemical Formula I, a pharmaceutically acceptable salt thereof, or a hydrate or solvate thereof in an effective amount to a mammal subject including a human in need thereof.

According to example embodiments of the present invention, new therapeutic agents for osteoporosis is designed and is synthesized in the present invention. It is confirmed that the new therapeutic agents (these compounds) are inhibitory of osteoclast differentiation (osteoclast formation), thus effectively suppressing bone resorption. The compound of Chemical Formula I, a pharmaceutically acceptable salt thereof, or a hydrate or solvate thereof are inhibitory of osteoclast differentiation, thus suppressing bone resorption. Thus, the compound of the present invention (the compound of Chemical Formula I), a pharmaceutically acceptable salt thereof, or a hydrate or solvate thereof has shown outstanding effects as an agent for alleviating, preventing or treating osteoporosis.

BRIEF DESCRIPTION OF THE DRAWINGS

The present invention will be more clearly understood from the following detailed description taken in conjunction with the accompanying drawings.

FIG. 1 is a graph showing MIT assay results of K11 and K22 compounds;

FIG. 2 is a graph showing MTT assay results of K14, K17, K18 and K19 compounds;

FIG. 3 is views showing effects of K11 compound on the expression of calcitonin receptor, cathepsin K, αv-integrin, β3-integrin, ATP6v0d2, and DC-STAMP;

FIG. 4 is a view showing the effect of K11 compound on the expression of NFATc1; and FIG. 5 is a view showing the effect of K11 compound on the expression of c-fos.

DESCRIPTION OF THE EMBODIMENTS

Figure 1:
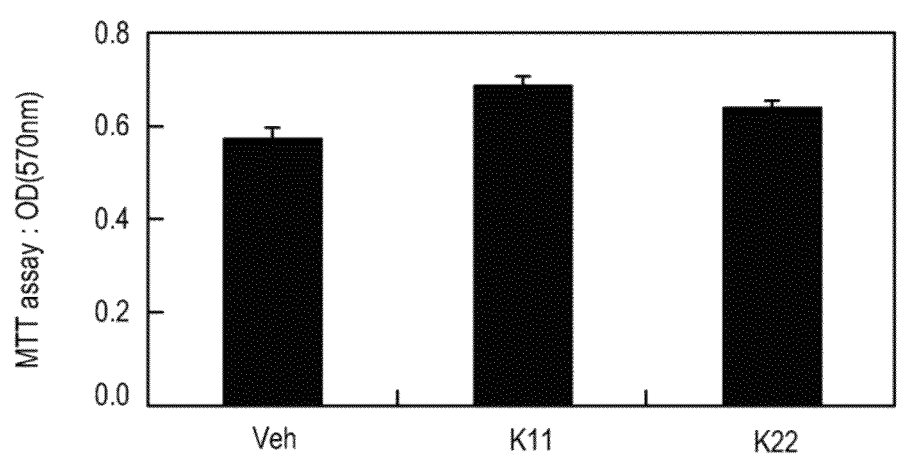
FIGS. 1-5 represent non-limiting, example embodiments as described herein.

Example embodiments of the present inventive concept may, however, be embodied in many different forms. Example embodiments will be described more fully hereinafter. It is understood that the present invention should not be limited to particular embodiments but various changes and modifications can be made by one ordinary skilled in the art within the spirit and scope of the present invention.

The terminology used herein is for the purpose of describing particular embodiments and is not intended to be limiting of the invention.

It will be understood that, although the terms first, second, etc., may be used herein to describe various elements, these elements should not be limited by these terms. These terms are used to distinguish one element from another. The terminology used herein is for the purpose of describing particular embodiments and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which the present invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The present invention now will be described more fully hereinafter with reference to the accompanying drawings.

The present invention provides a novel compound represented by the following Chemical Formula I, a pharmaceutically acceptable salt thereof, or a hydrate or solvate thereof:

[Chemical Formula I]

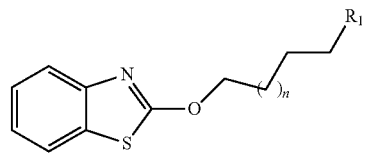

wherein,
n is 1 or 2, and
$R_1$ is fluoro, chloro, bromo, iodo,

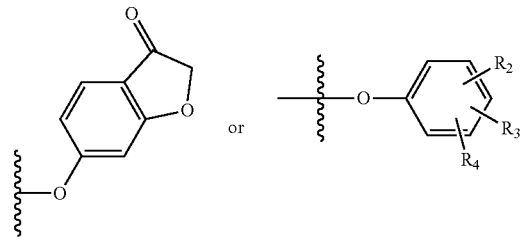

wherein $R_2$, $R_3$ and $R_4$ may be independently bonded to at least one of the carbon atoms of the phenyl ring at ortho-, meta- or para-position to the carbon atom to which the oxygen atom is attached, and is independently a hydrogen atom, fluoro, chloro, bromo, iodo, cyano, nitro, C1-4 alkyl, C1-4 alkoxy, C2-4 alkenyl, triazole, piperidine, pyridine or

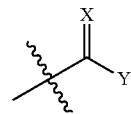

wherein X is —NOH, —NH.HCl, O or S and Y is —NR$_5$R$_6$ or —OR$_7$ wherein $R_5$, $R_6$ and $R_7$ are independently a hydrogen atom or C1-4 alkyl.

Preferable is a compound of the present invention (compound represented by Chemical Formula 1) in which n is 1 or 2, $R_1$ is chloro,

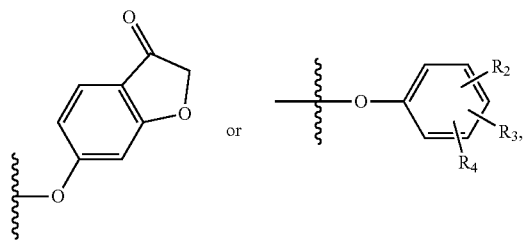

wherein $R_2$, $R_3$ and $R_4$ may be independently bonded to at least one of the carbon atoms of the phenyl ring at ortho-, meta- or para-position to the carbon atom to which the oxygen atom is attached, and is independently a hydrogen atom, fluoro, chloro, bromo, iodo, cyano, C1-4 alkyl, C1-4 alkoxy, triazole, or

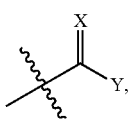

wherein X is —NOH, —NH.HCl or O and Y is NR₅R₆ or —OR₇, wherein R₅, R₆ and R₇ are independently an hydrogen atom or C1-4 alkyl, or a pharmaceutically acceptable salt thereof.

A compound of the present invention (compound represented by Chemical Formula 1), a pharmaceutically acceptable salt thereof, or a hydrate or solvate thereof is more preferably selected from the group consisting of:
2-(5-chloropentyloxy)benzo[d]thiazole,
2-(5-phenoxypentyloxy)benzo[d]thiazole,
4-(5-(benzo[d]thiazol-2-yloxy)pentyloxy)benzonitrile,
4-(5-(benzo[d]thiazol-2-yloxy)pentyloxy)-N-hydroxybenzamidine,
4-(5-(benzo[d]thiazol-2-yloxy)pentyloxy)benzamidine HCl,
methyl 4-(5-(benzo[d]thiazol-2-yloxy)pentyloxy)-3-methoxybenzoate,
4-(5-(benzo[d]thiazol-2-yloxy)pentyloxy)-3-methoxybenzoic acid,
4-(5-(benzo[d]thiazol-2-yloxy)pentyloxy)-N,N-diisopropyl-3-methoxy benzamide,
4-(5-(benzo[d]thiazol-2-yloxy)pentyloxy)-N,N-diethyl-3-methoxybenzamide,
2-(5-(3,5-dimethylphenoxy)pentyloxy)benzo[d]thiazole,
2-(5-(4-(1H-1,2,4-thiazol-1-yl)phenoxy)pentyloxy)benzo[d]thiazole,
2-(5-(4-fluorophenoxy)pentyloxy)benzo[d]thiazole,
2-(5-(3-chlorophenoxy)pentyloxy)benzo[d]thiazole,
6-(5-(benzo[d]thiazol-2-yloxy)pentyloxy)benzofuran-3(2H)-one,
2-(5-(2-methoxyphenoxy)pentyloxy)benzo[d]thiazole,
2-(5-(2-fluorophenoxy)pentyloxy)benzo[d]thiazole,
2-(4-chlorobutoxy)benzo[d]thiazole,
2-(4-phenoxybutoxy)benzo[d]thiazole,
4-(4-(benzo[d]thiazol-2-yloxy)butoxy)benzonitrile,
4-(4-(benzo[d]thiazol-2-yloxy)butoxy)-N-hydroxybenzamidine,
4-(4-(benzo[d]thiazol-2-yloxy)butoxy)-N,N-diisopropyl-3-methoxybenzamide, pharmaceutically acceptable salts thereof and a hydrate and solvate thereof,
with more preference for 4-(5-(benzo[d]thiazol-2-yloxy)pentyloxy)-N,N-diisopropyl-3-methoxybenzamide,
2-(5-(3-chlorophenoxy)pentyloxy)benzo[d]thiazole,
2-(5-(2-methoxyphenoxy)pentyloxy)benzo[d]thiazole,
2-(5-(2-fluorophenoxy)pentyloxy)benzo[d]thiazole,
2-(4-phenoxybutoxy)benzo[d]thiazole, and
4-(4-(benzo[d]thiazol-2-yloxy)butoxy)-N,N-diisopropyl-3-methoxybenzamide, pharmaceutically acceptable salts thereof, and a hydrate and solvate thereof and
most preference for 4-(5-(benzo[d]thiazol-2-yloxy)pentyloxy)-N,N-diisopropyl-3-methoxybenzamide, and
4-(4-(benzo[d]thiazol-2-yloxy)butoxy)-N,N-diisopropyl-3-methoxybenzamide, pharmaceutically acceptable salts thereof, and a hydrate and solvate thereof.

As used herein, the pharmaceutically acceptable salts is intended to refer to salts of inorganic or organic acid salts that are usually used for the preparation of medications. By way of examples, hydrochloric acid, bromic acid, sulfuric acid and phosphoric acid may be used as the inorganic acids. Exemplary among the organic acids useful in the present invention are citric acid, acetic acid, lactic acid, tartaric acid, fumaric acid, formic acid, propionic acid, oxalic acid, trifluoroacetic acid, methanesulfonic acid, benzenesulfonic acid, maleic acid, benzoic acid, gluconic acid, glycolic acid, succinic acid, 4-morpholine ethanesulfonic acid, camphorsulfonic acid, 4-nitrobenzenesulfonic acid, hydroxy-O-sulfonic acid, 4-toluene sulfonic acid, galacturonic acid, embonic acid, glutamic acid, and aspartic acid.

The present invention also provides a method for preparing the compound of Chemical Formula 1, comprising:
a) reacting 2-hydroxybenzothiazole with 1-bromo-5-chloropentane or 1-bromo-4-chlorobutane in the presence of a base to give a compound represented by the following Chemical Formula II and
b) reacting the compound of Chemical Formula II with a compound represented by the following Chemical Formula III in the presence of a base to synthesize the compound of Chemical Formula I:

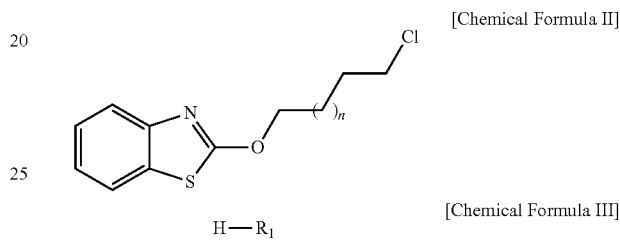

wherein,
n is 1 or 2, and
R₁ is

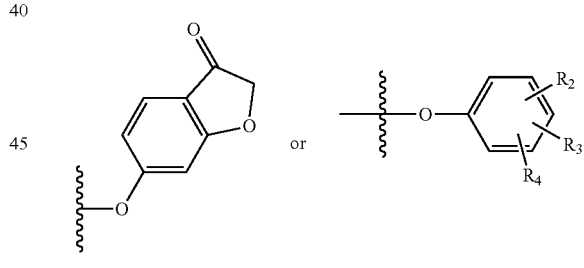

wherein R₂, R₃ and R₄ may be independently bonded to at least one of the carbon atoms of the phenyl ring at ortho-, meta- or para-position to the carbon atom to which the oxygen atom is attached, and is independently a hydrogen atom, fluoro, chloro, bromo, iodo, cyano, nitro, C1-4 alkyl, C1-4 alkoxy, C2-4 alkenyl, triazole, piperidine, pyridine or

wherein X is —NOH, —NH.HCl, O or S and Y is NR₅R₆ or —OR₇, wherein R₅, R₆ and R₇ are independently an hydrogen atom or C1-4 alkyl.

In step a) of the method of the present invention, starting materials 2-hydroxybenzothiazole, 1-bromo-5-chloropentane or 1-bromo-4-chlorobutane may be such those as are commercially available. In step a), 2-hydroxybenzothiazole is reacted with at a molar ratio of about 1:0.8~1.5 with 1-bromo-5-chloropentane or 1-bromo-5-chlorobutane and preferably at a molar ratio of about 1:1 with 1-bromo-5-chloropentane or 1-bromo-5-chlorobutane in terms of the prevention of side reactions, and economy.

In the method of the present invention, the base used in step a) is preferably selected from among potassium carbonate, sodium carbonate, calcium carbonate, sodium phosphate or a mixture thereof. It is preferably used in an amount of from about 1 to 2 moles per mole of 2-hydroxybenzothiazole.

The reaction of step a) may be conducted in a typical organic solvent, non-limiting illustrative examples of which include acetonitrile, DMF (dimethylformamide), DMSO (dimethylsulfoxide), acetone or a mixture thereof. Its amount may preferably be about 2 to 20 times as large in volume or weight as that of the starting material 2-hydroxybenzothiazole.

A reaction temperature for step a) may be between room temperature and the reflux temperature of the reaction solvent and preferably from about 50 to 90° C. The reaction where the solvent is acetonitrile is preferably performed at a temperature of approximately 75 to 95° C.

In step b) of the method of the present invention, the compound of Chemical Formula II is preferably reacted at a molar ratio of about 1:0.8~1.3 with the compound of Chemical Formula III and more preferably at a molar ratio of about 1:1 with the compound of Chemical Formula III.

The base used in step b) is preferably selected from among sodium hydroxide, potassium hydroxide, sodium carbonate, calcium carbonate, sodium phosphate or a mixture thereof. It is used in an amount of 1~2 moles per mole of the compound of Chemical Formula III.

A typical organic solvent may be useful as a reaction solvent for step b) and may be, for example, dimethylformamide, DMSO (dimethylsulfoxide), acetone or a mixture thereof. Its amount is preferably about 2 to 20 times as large in volume or weight as that of the compound of Chemical Formula II.

The reaction temperature for step b) may be between room temperature and the reflux temperature of the reaction solvent and preferably from about 50 to 90° C. When the solvent is dimethylformamide, the reaction is performed at a temperature of approximately 75 to 95° C.

The present invention also provides a composition for the alleviation, prevention or treatment of osteoporosis, comprising a novel compound represented by the following Chemical Formula 1, a pharmaceutically acceptable salt thereof, or a hydrate or solvate thereof in an effective amount:
wherein,
n is 1 or 2,
$R_1$ is fluoro, chloro, bromo, iodo,

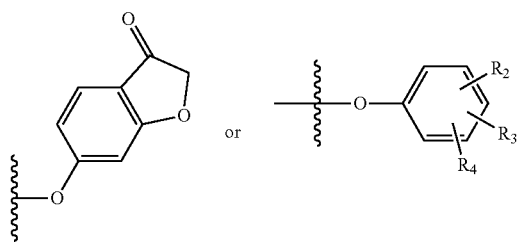

wherein $R_2$, $R_3$ and $R_4$ may be independently bonded to at least one of the carbon atoms of the phenyl ring at ortho-, meta- or para-position to the carbon atom to which the oxygen atom is attached, and is independently a hydrogen atom, fluoro, chloro, bromo, iodo, cyano, nitro, C1-4 alkyl, C1-4 alkoxy, C2-4 alkenyl, triazole, piperidine, pyridine or

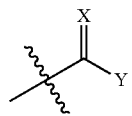

wherein X is —NOH, —NH.HCl, O or S and Y is —NR$_5$R$_6$ or —OR$_7$ wherein $R_5$, $R_6$ and $R_7$ are independently a hydrogen atom or C1-4 alkyl.

Preferable is a compound represented by Chemical Formula 1 as an active ingredient in which n is 1 or 2, $R_1$ is chloro,

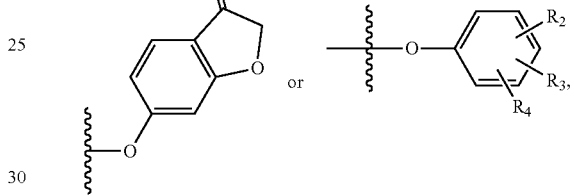

wherein $R_2$, $R_3$ and $R_4$ may be independently bonded to at least one of the carbon atoms of the phenyl ring at ortho-, meta- or para-position to the carbon atom to which the oxygen atom is attached, and is independently a hydrogen atom, fluoro, chloro, bromo, iodo, cyano, C1-4 alkyl, C1-4 alkoxy, triazole, or

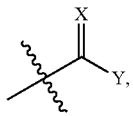

wherein X is —NOH, —NH. HCl or O and Y is NR$_5$R$_6$ or —OR$_7$, wherein $R_5$, $R_6$ and $R_7$ are independently an hydrogen atom or C1-4 alkyl.

In the composition of the present invention, the compound of Chemical Formula I, a pharmaceutically acceptable salt thereof, or a hydrate or solvate thereof is more preferably selected from the group consisting of: 2-(5-chloropentyloxy)benzo[d]thiazole,
2-(5-phenoxypentyloxy)benzo[d]thiazole,
4-(5-(benzo[d]thiazol-2-yloxy)pentyloxy)benzonitrile,
4-(5-(benzo[d]thiazol-2-yloxy)pentyloxy)-N-hydroxybenzamidine,
4-(5-(benzo[d]thiazol-2-yloxy)pentyloxy)benzamidine HCl,
methyl 4-(5-(benzo[d]thiazol-2-yloxy)pentyloxy)-3-methoxybenzoate,
4-(5-(benzo[d]thiazol-2-yloxy)pentyloxy)-3-methoxybenzoic acid,
4-(5-(benzo[d]thiazol-2-yloxy)pentyloxy)-N,N-diisopropyl-3-methoxy benzamide,
4-(5-(benzo[d]thiazol-2-yloxy)pentyloxy)-N,N-diethyl-3-methoxybenzamide, 2-(5-(3,5-dimethylphenoxy)pentyloxy)benzo[d]thiazole,
2-(5-(4-(1H-1,2,4-thiazol-1-yl)phenoxy)pentyloxy)benzo[d]thiazole,
2-(5-(4-fluorophenoxy)pentyloxy)benzo[d]thiazole,
2-(5-(3-chlorophenoxy)pentyloxy)benzo[d]thiazole,
6-(5-(benzo[d]thiazol-2-yloxy)pentyloxy)benzofuran-3(2H)-one,
2-(5-(2-methoxyphenoxy)pentyloxy)benzo[d]thiazole,
2-(5-(2-fluorophenoxy)pentyloxy)benzo[d]thiazole,
2-(4-chlorobutoxy)benzo[d]thiazole,
2-(4-phenoxybutoxy)benzo[d]thiazole,
4-(4-(benzo[d]thiazol-2-yloxy)butoxy)benzonitrile,
4-(4-(benzo[d]thiazol-2-yloxy)butoxy)-N'-hydroxybenzamidine,
4-(4-(benzo[d]thiazol-2-yloxy)butoxy)-N,N-diisopropyl-3-methoxybenzamide,
pharmaceutically acceptable salts thereof, and a hydrate or solvate thereof.

More preferable are 4-(5-(benzo[d]thiazol-2-yloxy)pentyloxy)-N,N-diisopropyl-3-methoxybenzamide,
2-(5-(3-chlorophenoxy)pentyloxy)benzo[d]thiazole,
2-(5-(2-methoxyphenoxy)pentyloxy)benzo[d]thiazole,
2-(5-(2-fluorophenoxy)pentyloxy)benzo[d]thiazole,
2-(4-phenoxybutoxy)benzo[d]thiazole,
4-(4-(benzo[d]thiazol-2-yloxy)butoxy)-N,N-diisopropyl-3-methoxybenzamide, pharmaceutically acceptable salts thereof, and a hydrate and solvate thereof.

Most preferable are 4-(5(benzo[d]thiazol-2-yloxy)pentyloxy)-N,N-diisopropyl-3-methoxybenzamide,
4-(4-(benzo[d]thiazol-2-yloxy)butoxy)-N,N-diisopropyl-3-methoxybenzamide, pharmaceutically acceptable salts thereof, and a hydrate and solvate thereof.

The present invention provides a method for alleviating, preventing or treating osteoporosis, comprising administering the above mentioned compound of Chemical Formula I in an effective amount to a mammal subject including a human in need thereof:

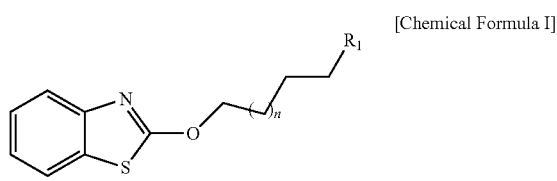

[Chemical Formula I]

wherein,
n is 1 or 2,
$R_1$ is chloro,

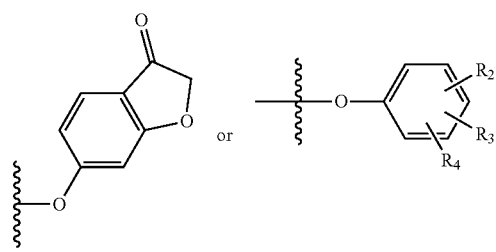

or wherein $R_2$, $R_3$ and $R_4$ may be independently bonded to at least one of the carbon atoms of the phenyl ring at ortho-, meta- or para-position to the carbon atom to which the oxygen atom is attached, and is independently a hydrogen atom, fluoro, chloro, bromo, iodo, cyano, nitro, C1-4 alkyl, C1-4 alkoxy, C2-4 alkenyl, triazole, piperidine, pyridine or

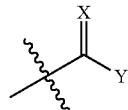

wherein X is —NOH, —NH.HCl, O or S and Y is —NR$_5$R$_6$ or —OR$_7$ wherein R$_5$, R$_6$ and R$_7$ are independently a hydrogen atom or C1-4 alkyl.

In the method of the present invention, the compound of Chemical Formula I, a pharmaceutically acceptable salt thereof, or a hydrate or solvate thereof is preferably selected from the group consisting of
2-(5-chloropentyloxy)benzo[d]thiazole,
2-(5-phenoxypentyloxy)benzo[d]thiazole,
4-(5-(benzo[d]thiazol-2-yloxy)pentyloxy)benzonitrile,
4-(5-(benzo[d]thiazol-2-yloxy)pentyloxy)-N-hydroxybenzamidine,
4-(5-(benzo[d]thiazol-2-yloxy)pentyloxy)benzamidine HCl,
methyl 4-(5-(benzo[d]thiazol-2-yloxy)pentyloxy)-3-methoxybenzoate,
4-(5-(benzo[d]thiazol-2-yloxy)pentyloxy)-3-methoxybenzoic acid,
4-(5-(benzo[d]thiazol-2-yloxy)pentyloxy)-N,N-diisopropyl-3-methoxy benzamide,
4-(5-(benzo[d]thiazol-2-yloxy)pentyloxy)-N,N-diethyl-3-methoxybenzamide,
2-(5-(3,5-dimethylphenoxy)pentyloxy)benzo[d]thiazole,
2-(5-(4-(1H-1,2,4-thiazol-1-yl)phenoxy)pentyloxy)benzo[d]thiazole,
2-(5-(4-fluorophenoxy)pentyloxy)benzo[d]thiazole,
2-(5-(3-chlorophenoxy)pentyloxy)benzo[d]thiazole,
6-(5-(benzo[d]thiazol-2-yloxy)pentyloxy)benzofuran-3(2H)-one,
2-(5-(2-methoxyphenoxy)pentyloxy)benzo[d]thiazole,
2-(5-(2-fluorophenoxy)pentyloxy)benzo[d]thiazole,
2-(4-chlorobutoxy)benzo[d]thiazole,
2-(4-phenoxybutoxy)benzo[d]thiazole,
4-(4-(benzo[d]thiazol-2-yloxy)butoxy)benzonitrile,
4-(4-(benzo[d]thiazol-2-yloxy)butoxy)-N-hydroxybenzamidine,
4-(4-(benzo[d]thiazol-2-yloxy)butoxy)-N,N-diisopropyl-3-methoxybenzamide,
pharmaceutically acceptable salts thereof, and a hydrate or solvate thereof,
with more preference for 4-(5-(benzo[d]thiazol-2-yloxy)pentyloxy)-N,N-diisopropyl-3-methoxybenzamide,
2-(5-(3-chlorophenoxy)pentyloxy)benzo[d]thiazole,
2-(5-(2-methoxyphenoxy)pentyloxy)benzo[d]thiazole,
2-(5-(2-fluorophenoxy)pentyloxy)benzo[d]thiazole,
2-(4-phenoxybutoxy)benzo[d]thiazole, and
4-(4-(benzo[d]thiazol-2-yloxy)butoxy)-N,N-diisopropyl-3-methoxybenzamide, pharmaceutically acceptable salts thereof, and a hydrate and solvate thereof and
most preference for 4-(5-(benzo[d]thiazol-2-yloxy)pentyloxy)-N,N-diisopropyl-3-methoxybenzamide, and
4-(4-(benzo[d]thiazol-2-yloxy)butoxy)-N,N-diisopropyl-3-methoxybenzamide, pharmaceutically acceptable salts thereof, and a hydrate and solvate thereof. The present invention also provides the use of the above mentioned compound of Chemical Formula I in preparing a pharmaceutical preparation for the prevention or treatment of osteoporosis.

As used herein, the term "osteoporosis" is a disease of bones in which the bones become porous like a sponge as a result of excessive loss of the bone minerals and matrix and are highly apt to be fractured.

The composition of the present invention may comprise at least one functionally identical or similar ingredient in addition the compound of Chemical Formula I, a pharmaceutically acceptable salt thereof, or a hydrate or solvate thereof.

For administration, the composition of the present invention may further comprise at least one pharmaceutically acceptable carrier. Examples of the pharmaceutically acceptable carrier include physiological saline, sterile water, Ringer's solution, buffered saline, a dextrose solution, a maltodextrin solution, glycerol, ethanol and a combination thereof. If necessary, a typical excipient such as an antioxidant, buffer, a bacteriostatic agent, etc. may be added. Moreover, a diluent, a dispersant, a surfactant, a binder and/or a lubricant may be added to the composition to formulate a injection such as an aqueous solution, a suspension, an emulsion, etc., a pill, a capsule, a granule, or a tablet. Further, the composition may be formulated into suitable dosage forms according to disease or ingredient using a method known in the art or to disclosed in Remington's Pharmaceutical Science (latest version), Mack Publishing Company, Easton Pa. According to the purpose, the composition of the present invention may be administered into humans or animals orally or parenterally (for example, intravenously, subcutaneously, intraperitoneally or topically). The effective dose of the composition is dependent on various factors including the patient's weight, age, sex, general health state and diet, the time and route of administration, excrement rate, and the severity of disease. The composition may be administered in a single dose or it may be spread out over multiple doses per day, with the daily dose ranging from about 10 to 1,0000 mg/kg and preferably from 50 to 500 mg/kg.

For the effective prophylaxis and treatment of osteoporosis, the composition according to the present invention may be used alone or in combination with surgical operation, hormonal therapy, drug therapy, and/or biological response controllers.

Hereinafter, preferred Examples and Experimental Examples are provided for illustrating the present invention. However, it should be understood that the following Examples and Experimental Examples are provided only for illustrating the present invention and should not be construed as limiting the scope and spirit of the present invention.

Reagents and solvents used in the following Examples were purchased from Aldrich unless stated otherwise. $^1$H-NMR data were measurements made by 400 MHz Varian FT-NMR spectrometer and Mass data was read on JMS-700 (Jeol, Japan).

Example 1

Synthesis of 2-(5-Chloropentyloxy)benzo[d]thiazole (K23)

To a solution of 2-hydroxybenzothiazole (0.2 g, 1.32 mmol) in 10 mL of acetonitrile was added $K_2CO_3$ (0.274 g, 1.98 mmol), followed by stirring at 50~55° C. for 30 min. Then, 1-bromo-5-chloropentane (0.245 g, 1.32 mmol) was added to and reacted with the solution of 2-hydroxybenzothiazole at 80~90° C. for 3 hours. The reaction was cooled to room temperature, diluted with 10 mL of EtOAc, and washed with distilled water and a saturated NaCl aqueous solution. It was dried over $MgSO_4$ and the solvent was removed by concentration under reduced pressure to afford K23 (0.333 g, 98%).

Transparent oil; $^1$H NMR (400 MHz, Acetone-d$_6$) δ 7.579 (d, J=7.8, 1H), 7.393~7.295 (m, 2H), 7.194 (t, J=7.5, 1H), 4.015 (t, J=7.2, 2H), 3.602 (t, J=6.6, 2H), 1.869~1.743 (m, 4H), 1.574~1.496 (m, 2H); HR-FABMS Calcd for $C_{12}H_{15}ClNOS$ (M$^+$+H): 256.0563. Found: 256.0565.

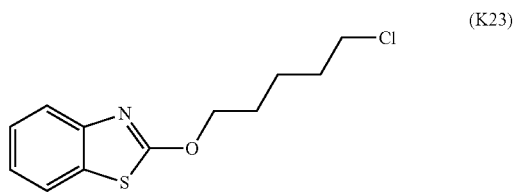 [SMILES: ClCCCCCOc1nc2ccccc2s1]

(K23)

Example 2

Synthesis of 2-(5-Phenoxypentyloxy)benzo[d]thiazole (K16)

To phenol (0.018 g, 0.20 mmol) in 3 mL of DMF was added NaOH (0.012 g, 0.29 mmol), followed by stirring at 50~55° C. for 30 min. This solution was mixed and reacted with K23 (0.05 g, 0.20 mmol) in 3 mL of DMF at 80~90° C. for 3 hours. The reaction was cooled to room temperature, diluted with 6 mL of EtOAc, and washed with distilled water and a saturated NaCl aqueous solution. It was dried over $MgSO_4$ and the solvent was removed by concentration under reduced pressure. Recrystallization in ethanol afforded K16 (0.014 g, 24%).

White powder, mp 73~74 □; 1H NMR (400 MHz, Acetone-d6) δ 7.595 (d, J=7.9, 1H), 7.398~7.317 (m, 2H), 7.276~7.236 (m, 2H), 7.201 (t, J=7.5, 1H), 6.921~6.875 (m, 3H), 4.048 (t, J=7.2, 2H), 3.997 (t, J=6.4, 2H), 1.882~1.802 (m, 4H), 1.624~1.566 (m, 2H); HR-FABMS Calcd for $C_{18}H_{20}NO_2S$ (M$^+$+H): 314.1215. Found: 314.1219.

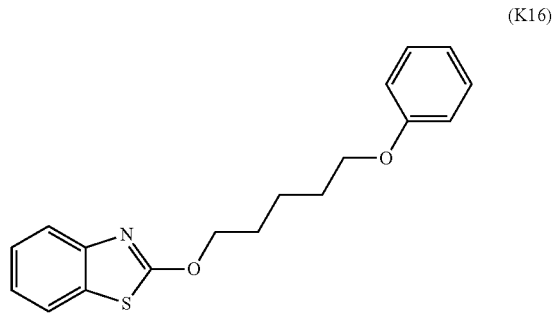 [SMILES: c1ccc(OCCCCCOc2nc3ccccc3s2)cc1]

(K16)

Example 3

Synthesis of 4-(5-(Benzo[d]thiazol-2-yloxy)pentyloxy)benzonitrile (K3)

4-cyanophenol (0.047 g, 0.39 mmol), NaOH (0.024 g, 0.59 mmol), and K23 compound (0.1 g, 0.39 mmol) were reacted in the same manner as in Example 2, followed by recrystallization in ethanol to afford K3 compound (0.070 g, 53%).

White powder, mp 98~101 □; 1H NMR (400 MHz, Acetone-d6) δ 7.679 (d, J=9.2, 2H), 7.596 (d, 1H), 7.396~7.310 (m, 2H), 7.203 (t, J=7.5, 1H), 7.090 (d, 2H), 4.125 (t, J=6.6, 2H), 4.048 (t, J=7.2, 2H), 1.906~1.826 (m, 4H), 1.627~1.550 (m, 2H); HR-FABMS Calcd for $C_{19}H_{19}N_2O_2S$ ($M^+$+H): 339.1167. Found: 339.1162.

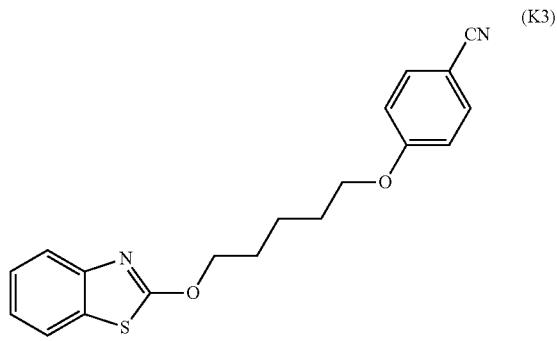 [SMILES: N#Cc1ccc(OCCCCCOc2nc3ccccc3s2)cc1]

(K3)

Example 4

Synthesis of 4-(5-(Benzo[d]thiazol-2-yloxy)pentyloxy)-N-hydroxybenzamidine (K4)

Triethylamine (0.032 g, 0.31 mmol) was added to K3 compound (0.053 g, 0.16 mmol) in 10 ml of ethanol with stirring. The solution was mixed with NH₂OH.HCl (0.022 g, 0.31 mmol) and refluxed overnight. Then, the reaction was cooled to 40° C. before slowly adding distilled water thereto to form a crystal. It was washed with distilled water and ether to afford the title compound K4 (0.029 g, 49%).

White powder, mp 144~447 □; 1H NMR (400 MHz, Acetone-d₆) δ 8.695 (s, 1H), 7.629 (d, J=8.8, 2H), 7.594 (d, J=7.6, 1H), 7.398~7.314 (m, 2H), 7.200 (t, J=7.6, 1H), 6.898 (d, J=8.8, 2H), 5.343 (s, 2H), 4.066~4.012 (m, 4H), 1.890~4.803 (m, 4H), 1.611~1.566 (m, 2H); HR-FABMS Calcd for $C_{19}H_{22}N_3O_3S$ ($M^+$+H): 372.1382. Found: 372.1377.

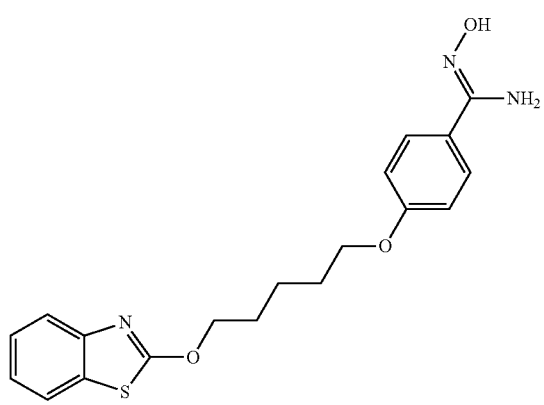

(K4)

Example 5

Synthesis of 4-(5-(benzo[d]thiazol-2-yloxy)pentyloxy)benzamidine hydrochloride (K5)

In a flask was put 0.2 mL of 1M LiN(SiMe₃)₂THF. A solution of K3 (0.05 g, 0.15 mmol) in 2 mL of dry THF was added to the flask purged with nitrogen gas and stirred at room temperature for 4 hours. To the flask was added 0.1 mL of 6 NHCl iPrOH before storage in a freezer overnight. The crystals thus formed were washed with ether. Filtration under reduced pressure afforded K5 compound (0.008 g; 14%).

Pale yellow powder, mp 245~247 □; 1H NMR (Free base, 400 MHz, DMSO) δ 9.080 (brs, 3H), 7.807 (d, J=8.4, 2H), 7.663 (d, J=8.0, 1H), 7.380 (d, 2H), 7.226~7.196 (m, 1H), 7.121 (d, J=8.8, 2H), 4.068 (t, J=6.4, 2H), 3.983 (t, J=7.2, 2H), 1.799~1.704 (m, 4H), 1.479~1.461 (m, 2H); HR-FABMS Calcd for $C_{19}H_{22}N_3O_2S$ ($M^+$+H): 356.1433. Found: 356.1435.

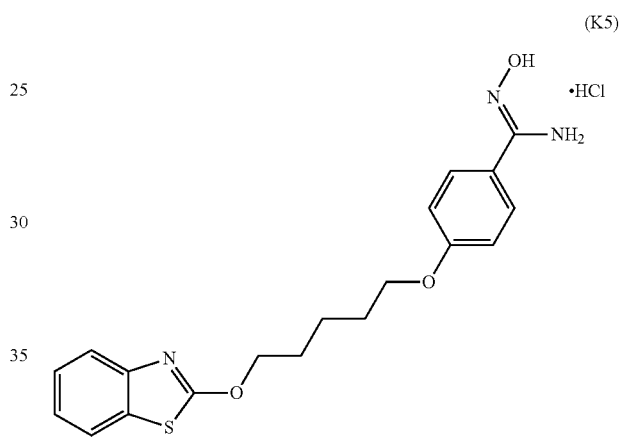

(K5)

Example 6

Synthesis of Methyl 4-(5-(benzo[d]thiazol-2-yloxy)pentyloxy-3-methoxybenzoate} (K9)

(1) Synthesis of methyl 4-hydroxy-3-methoxybenzoate (9)

To a solution of 4-hydroxy-3-methoxybenzoic acid (0.1 g, 0.59 mmol) in 10 mL of methanol was added 0.3 mL of conc. sulfuric acid, and refluxed overnight. The pH of the solution was shifted into an alkaline zone by addition of 5% aqueous NaHCO₃ solution. Following extraction with EtOAc, the extract was washed with a saturated NaCl aqueous solution. It was dried over MgSO₄ and the solvent was removed by concentration under reduced pressure to afford the compound 9 (0.107 g, 98%).

Yellow oil; ¹H NMR (400 MHz, Acetone-d₆) δ 8.390 (s, 1H), 7.561 (d, J=8.0, 7.538 (s, 1H), 6.911 (d, J=8.4, 1H), 6.516 (s, 2H), 3.904 (s, 3H), 3.831 (s, 3H).

(2) Synthesis of Methyl 4-(5-(benzo[d]thiazol-2-yloxy)pentyloxy)-3-methoxybenzoate (K9)

The compound 9 (0.043 g, 0.39 mmol) in 3 mL of acetonitrile was mixed with K₂CO₃ (0.027 g, 0.20 mmol) at 50~55° C. for 30 min by stirring. To this solution was added K23 compound (0.05 g, 0.20 mmol) in 3 mL of acetonitrile, followed by reaction at 80° C. for two days.

The resulting mixture was cooled to room temperature, diluted with 6 mL of diethylether, and washed with distilled water and a saturated NaCl aqueous solution. It was dried over MgSO₄ and the solvent was removed by concentration under reduced pressure. Crystallization in diethylether and n-hexane afforded the K9 compound (0.017 g, 21%).

White powder, mp 68~70° C.; $^1$H NMR (400 MHz, Acetone-d$_6$) δ 7.598 (d, J=8.4, 2H), 7.509 (s, 1H), 7.394~7.315 (m, 2H), 7.199 (t, J=7.6, 1H), 7.032 (d, J=8.4, 1H), 4.099 (t, J=6.4, 2H), 4.051 (t, J=7.2, 2H), 3.838 (s, 6H), 1.931~1.818 (m, 4H), 1.643~1.584 (m, 2H); HR-FABMS Calcd for C$_{21}$H$_{24}$NO$_5$S (M$^+$+H): 402.1375. Found: 402.1377.

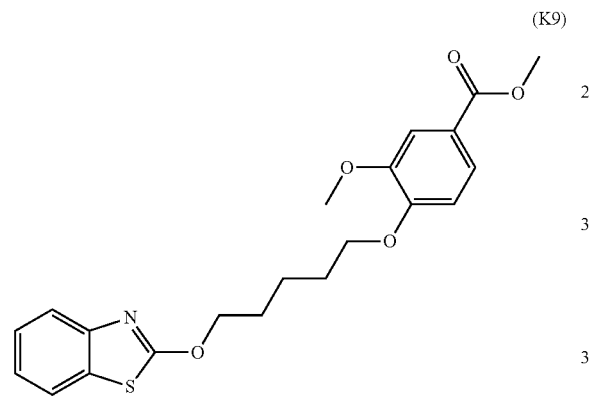 [SMILES: CCN(CC)C(=O)c1ccc(OCCCCCOc2nc3ccccc3s2)c(OC)c1]

(K9)

Example 7

Synthesis of 4-(5-(Benzo[d]thiazol-2-yloxy)pentyloxy)-3-methoxybenzoic acid (K10)

The reaction mixture of K9 compound reacted for two days was stirred and mixed overnight at room temperature with 7 mL of 2N NaOH. To this mixture were added distilled water and diethylether. The aqueous layer thus formed was separated from the organic layer and acidified with 10% aqueous solution of HCl to a pH of 2, followed by extraction with diethylether. The extract was washed with a saturated NaCl aqueous solution and dried over MgSO₄, and the solvent was removed by concentration under reduced pressure. Recrystallization in diethylether afforded the K10 compound (0.037 g, 48%).

White powder, mp 130~131° C.; $^1$H NMR (400 MHz, Acetone-d$_6$) δ 7.633 (d, J=8.4, 1H), 7.596 (d, J=7.8, 1H), 7.536 (s, 1H), 7.397~7.319 (m, 2H), 7.200 (t, J=7.6, 1H), 7.033 (d, J=8.4, 1H), 4.104 (t, J=6.4, 2H), 4.055 (t, J=7.2, 2H), 3.846 (s, 3H), 1.936~1.822 (m, 4H), 1.648~1.572 to (m, 2H); HR-FABMS Calcd for C$_{20}$H$_{22}$NO$_5$S (M$^+$+H): 388.1219. Found: 388.1213.

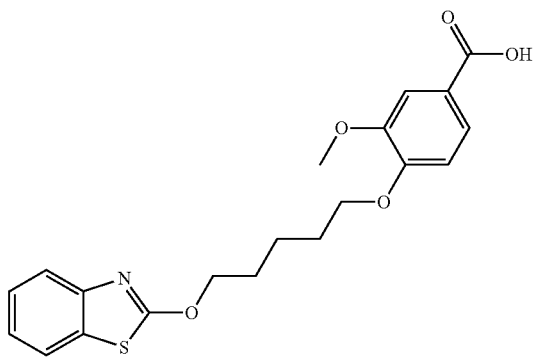

(K10)

Example 8

Synthesis of 4-(5-(Benzo[d]thiazol-2-yloxy)pentyloxy)-N,N-diisopropyl-3-methoxyBenzamide (K11)

(1) Synthesis of 4-Hydroxy-N,N-diisopropyl-3-methoxybenzamide(10)

A solution of 4-hydroxy-3-methoxybenzoic acid (0.1 g, 0.59 mmol) in 5 mL of dichloromethane was mixed with SOCl$_2$ (0.637 g, 5.35 mmol) and 0.025 mL of DMF in that order and refluxed for one hour. Following concentration under reduced pressure using a rotary evaporator, the residue was dissolved in 5 mL of dichloromethane, and then mixed with diisopropylamine (0.301 g, 2.97 mmol) in an ice bath. The mixture was stirred at room temperature for 2 hours, diluted with 5 mL of EtOAc and washed with 1N HCl aqueous solution, 1N NaOH aqueous solution and a saturated NaCl aqueous solution. It was dried over MgSO₄ and the solvent was removed by concentration under reduced pressure to afford the compound 10 (0.087 g, 58%).

Pale yellow powder; $^1$H NMR (400 MHz, Acetone-d$_6$) δ 7.267 (d, J=8.0, 1H), 7.071 (s, 1H), 6.919 (d, J=8.2, 1H), 3.878 (s, 3H), 3.726 (brs, 2H), 1.320 (brs, 12H).

(2) Synthesis of 4-(5-(Benzo[d]thiazol-2-yloxy)pentyloxy)-N,N-diisopropyl-3-methoxybenzamide (K11)

NaOH (0.010 g, 0.24 mmol) was added to a solution of the compound 10 (0.041 g, 0.16 mmol) in 6 mL of DMF and stirred at 50~55° C. for 30 min. This solution was mixed with the compound K23 (0.041 g, 0.16 mmol) in 3 mL of DMF and reacted at 80~90° C. for 4 hours. The reaction was cooled to room temperature, diluted with 6 mL of EtOAc and washed with distilled water and a saturated NaCl aqueous solution. It was dried over MgSO₄ and the solvent was removed by concentration under reduced pressure. Recrystallization in ethanol afforded the compound K11 (0.069 g, 91%).

Yellow oil; $^1$H NMR (400 MHz, Acetone-d$_6$) δ 7.595 (d, J=7.9, 1H), 7.399~7.305 (m, 2H), 7.201 (t, J=7.4, 1H), 6.939 (d, J=8.0, 1H), 6.882 (s, 1H), 6.823 (d, J=8.0, 1H), 4.071~4.013 (m, 4H), 3.802 (s, 3H), 3.742 (brs, 2H), 1.888~1.834 (m, 1.625~1.585 (m, 2H), 1.320 (brs, 12H); HR-FABMS Calcd for C$_{26}$H$_{35}$N$_2$O$_4$S (M$^+$+H): 471.2318. Found: 471.2321.

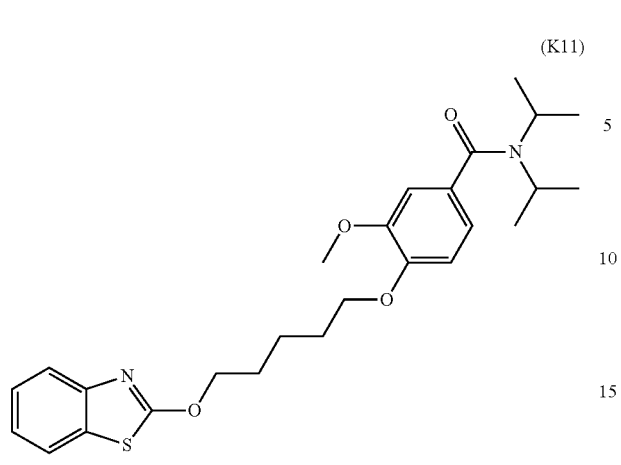

Example 9

Synthesis of 4-(5-(Benzo[d]thiazol-2-yloxy)pentyloxy)-N,N-diethyl-3-methoxybenzamide (K26)

Vanillic acid diethylamide (0.044 g, 0.20 mmol), NaOH (0.012 g, 0.29 mmol), and the compound K23 (0.05 g, 0.20 mmol) were reacted in the same manner as in Example 2 to afford the compound K26 as a yellow oil (0.083 g, 95%).

Yellow oil; $^1$H NMR (400 MHz, Acetone-$d_6$) 7.596 (d, J=7.7, 1H), 7.399~7.320 (m, 2H), 7.200 (t, J=7.5, 1H), 6.970~6.945 (m, 2H), 6.901 (d, J=8.0, 1H), 4.071~4.023 (m, 4H), 3.811 (s, 3H), 3.401~3.385 (m, 4H), 1.892~1.837 (m, 4H), 1.626~1.607 (m, 2H), 1.150 (t, J=7.2, 6H); HR-FABMS Calcd for $C_{24}H_{31}N_2O_4S$ (M$^+$+H): 443.2005. Found: 443.2008.

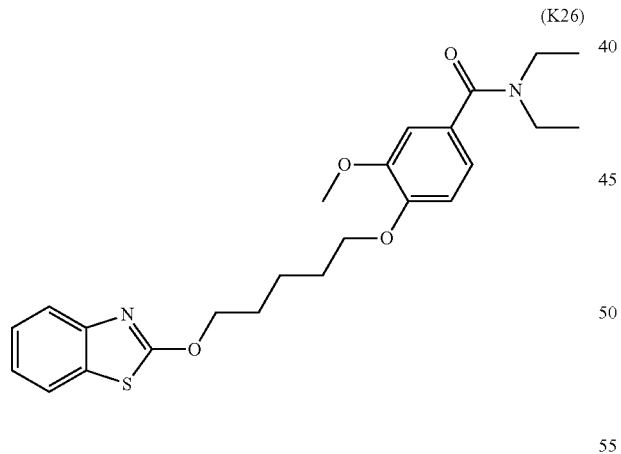

Example 10

Synthesis of 2-(5-(3,5-dimethylphenoxy)pentyloxy)benzo[d]thiazole (K8)

3,5-Dimethylphenol (0.40 g, 0.33 mmol), NaOH (0.020 g, 0.50 mmol), and the compound K23 (0.085 g, 0.33 mmol) were reacted for 4 hours in the same manner as in Example 2, and recrystallization in ethanol afforded the compound K8 (0.108 g, 96%).

White powder, mp 61~63° C.; $^1$H NMR (400 MHz, Acetone-$d_6$) δ 7.588 (d, J=7.7, 1H), 7.391~7.307 (m, 2H), 7.195 (t, J=7.5, 1H), 6.542 (s, 1H), 6.516 (s, 2H), 4.037 (t, J=7.4, 2H), 3.942 (t, J=6.4, 2H), 2.222 (s, 6H), 1.843~1.777 (m, 4H), 1.588~1.542 (m, 2H); HR-FABMS Calcd for $C_{20}H_{24}NO_2S$ (M$^+$+H): 342.1528. Found: 342.1530.

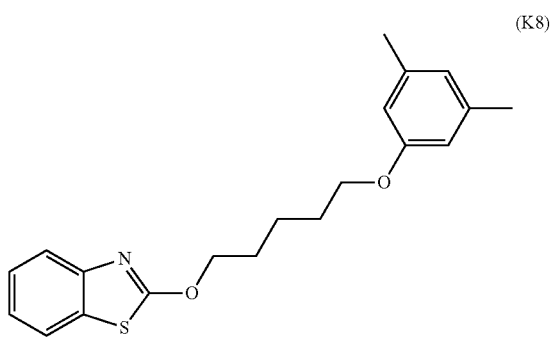 [SMILES: Cc1cc(C)cc(OCCCCCOc2nc3ccccc3s2)c1]

Example 11

Synthesis of 2-(5-(4-(1H-1,2,4-thiazol-1-yl)phenoxy)pentyloxy)benzo[d]thiazole (K12)

4-(1,2,4-thiazol-1-yl)phenol (0.032 g, 0.20 mmol), NaOH (0.012 g, 0.29 mmol), and the compound K23 (0.05 g, 0.20 mmol) were reacted in the same manner as in Example 2, and recrystallization in ethanol afforded the compound K12 (0.055 g, 74%).

White powder, mp 103~104° C.; $^1$H NMR (400 MHz, Acetone-$d_6$) δ 8.885 (s, 1H), 8.047 (s, 1H), 7.739 (d, J=9.2, 2H), 7.598 (d, J=7.8, 1H), 7.402~7.321 (m, 2H), 7.202 (t, J=7.5, 1H), 7.086 (d, J=8.8, 2H), 4.086 (t, J=6.4, 2H), 4.059 (t, J=7.4, 2H), 1.904~1.837 (m, 4H), 1.624~1.605 (m, 2H); HR-FABMS Calcd for $C_{20}H_{21}N_4O_2S$ (M$^+$+H): 381.1385. Found: 381.1386.

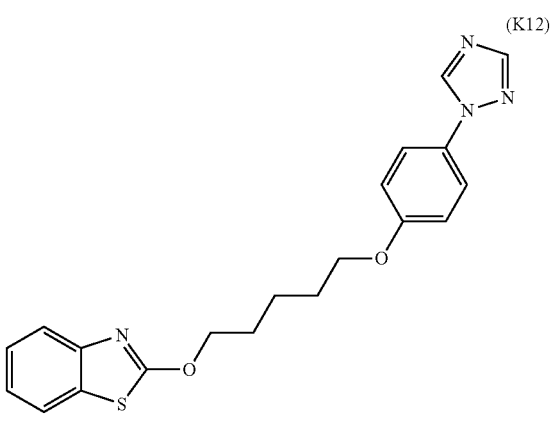 [SMILES: c1ccc2sc(OCCCCCOc3ccc(-n4cncn4)cc3)nc2c1]

Example 12

Synthesis of 2-(5-(4-Fluorophenoxy)pentyloxy)benzo[d]thiazole (K13)

4-Fluorophenol (0.022 g, 0.20 mmol), NaOH (0.012 g, 0.29 mmol), and the compound K23 (0.05 g, 0.20 mmol) were reacted in the same manner as in Example 2, and recrystallization in ethanol afforded the compound K13 (0.019 g, 30%).

White powder, mp 69~70° C.; $^1$H NMR (400 MHz, Acetone-$d_6$) δ 7.596 (d, J=7.8, 1H), 7.398~7.312 (m, 2H), 7.202 (t, J=7.5, 1H), 7.045~7.000 (m, 2H), 6.929~6.894 (m, 2H), 4.045 (t, J=7.4, 2H), 3.980 (t, J=6.4, 2H), 1.871~1.817 (m, 4H), 1.594~1.576 (m, 2H); HR-FABMS Calcd for $C_{18}H_{19}FNO_2S$ (M$^+$+H): 332.1121. Found: 332.1115.

7.392~7.311 (m, 2H), 7.199 (t, J=7.5, 1H), 6.693~6.665 (m, 2H), 4.637 (s, 2H), 4.147 (t, J=6.4, 2H), 3.053 (t, J=7.2, 2H), 1.942~1.809 (m, 4H), 1.636~1.558 (m, 2H); HR-FABMS Calcd for $C_{20}H_{20}NO_4S$ (M$^+$+H): 370.1113. Found: 370.1111.

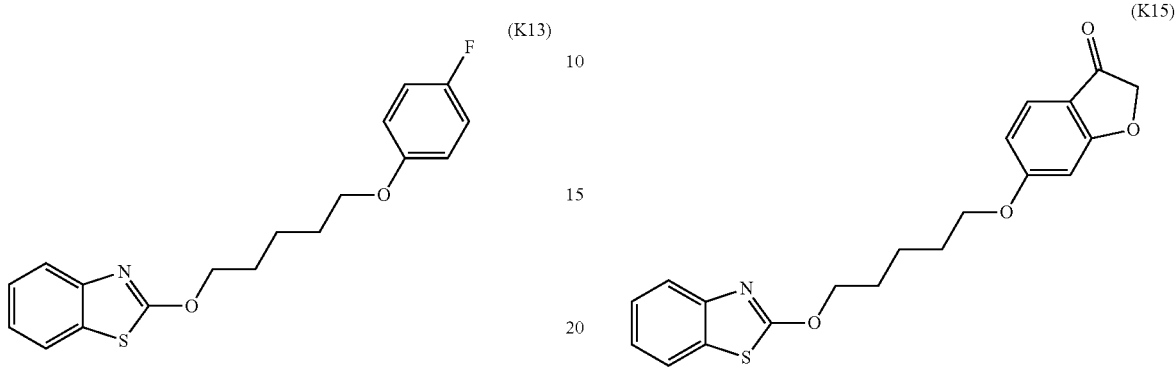

Example 13

Synthesis of 2-(5-(3-chlorophenoxy)pentyloxy)benzo[d]thiazole (K14)

3-Chlorophenol (0.025 g, 0.20 mmol), NaOH (0.012 g, 0.29 mmol), and the compound K23 (0.05 g, 0.20 mmol) were reacted in the same manner as in Example 2 to afford the compound K14 (0.041 g, 60%).

Yellow oil; $^1$H NMR (400 MHz, Acetone-$d_6$) δ 7.586 (d, J=7.8, 1H), 7.392~7.243 (m, 3H), 7.196 (t, J=7.5, 1H), 6.945~6.920 (m, 2H), 6.871 (d, J=8.4, 1H), 4.058~4.008 (m, 4H), 1.883~1.796 (m, 4H), 1.616~1.555 (m, 2H); HR-FABMS Calcd for $C_{18}H_{19}ClNO_2S$ (M$^+$+H): 348.0825. Found: 348.0824.

Example 15

Synthesis of 2-(5-(2-Methoxyphenoxy)pentyloxy)benzo[d]thiazole (K17)

Guaiacol (0.024 g, 0.20 mmol), NaOH (0.012 g, 0.29 mmol), and the compound K23 (0.05 g, 0.20 mmol) were reacted in the same manner as in Example 2, and recrystallization in diethylether afforded the compound K17 (0.064 g, 96%).

Yellow oil; $^1$H NMR (400 MHz, Acetone-$d_6$) δ 7.588 (d, J=8.0, 1H), 7.392~7.312 (m, 2H), 7.195 (t, J=7.4, 1H), 6.946~6.917 (m, 2H), 6.894~6.822 (m, 2H), 4.046 (t, J=7.2, 2H), 3.991 (t, J=6.4, 2H), 3.771 (s, 3H), 1.883~1.809 (m, 4H), 1.627~1.580 (m, 2H); HR-FABMS Calcd for $C_{19}H_{22}NO_3S$ (M$^+$+H): 344.1320. Found: 344.1317.

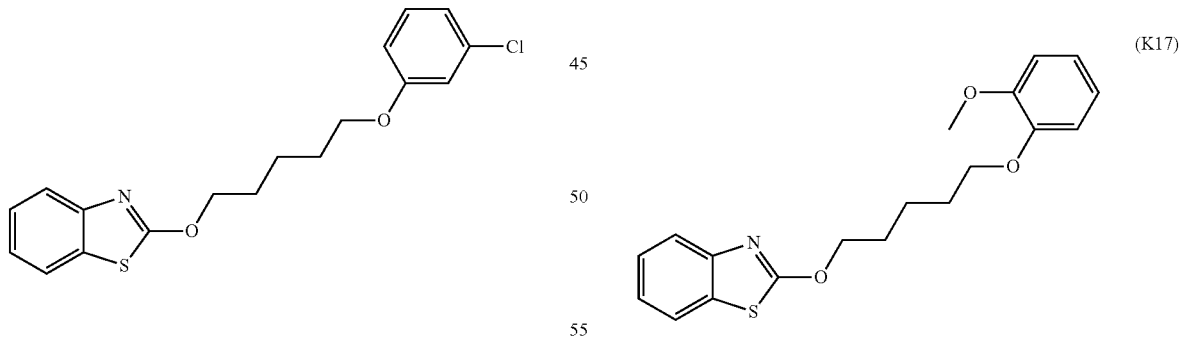

Example 14

Synthesis of 6-(5-(Benzo[d]thiazol-2-yloxy)pentyloxy)benzofuran-3(2H)-one] (K15)

6-hydroxy-3-coumaranone (0.029 g, 0.20 mmol), NaOH (0.012 g, 0.29 mmol), and the compound K23 (0.05 g, 0.20 mmol) were reacted in the same manner as in Example 2, and recrystallization in EtOAc and diethylether afforded the compound K15 (0.013 g, 18%).

Brown powder, mp 75~78° C.; $^1$H NMR (400 MHz, Acetone-$d_6$) δ 7.591 (d, J=7.9, 1H), 7.487 (d, J=9.2, 1H),

Example 16

Synthesis of 2-(5-(2-Fluorophenoxy)pentyloxy)benzo[d]thiazole] (K18)

2-Fluorophenol (0.022 g, 0.20 mmol), NaOH (0.012 g, 0.29 mmol), and the compound K23 (0.05 g, 0.20 mmol) were reacted in the same manner as in Example 2 to afford the compound K18 (0.057 g, 88%).

Yellow oil; $^1$H NMR (400 MHz, Acetone-$d_6$) δ 7.592 (d, J=7.6, 1H), 7.396~7.317 (m, 2H), 7.198 (t, J=7.5, 1H), 7.139~7.061 (m, 3H), 6.938~4.895 (m, 1H), 4.099~4.031 (m, 4H), 1.897~1.807 (m, 4H), 1.625~1.579 (m, 2H); HR-FABMS Calcd for $C_{18}H_{19}FNO_2S$ (M$^+$+H): 332.1121. Found: 332.1125.

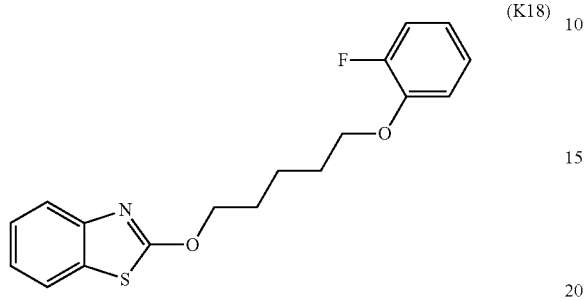

(K18)

Example 17

Synthesis of 2-(4-Chlorobutoxy)benzo[d]thiazole (K24)

2-hydroxybenzothiazole (0.2 g, 1.32 mmol) and 1-bromo-4-chlorobutane (0.227 g, 1.32 mmol) were reacted in the same manner as in Example 1 to afford the compound K24 (0.302 g, 94%).

Transparent oil; $^1$H NMR (400 MHz, Acetone-$d_6$) δ 7.602 (d, J=7.6, 1H), 7.410~7.325 (m, 2H), 7.210 (t, J=7.5, 1H), 4.065 (t, J=7.0, 2H), 3.685 (t, J=6.4, 2H), 1.920~1.857 (m, 4H); HR-FABMS Calcd for $C_{11}H_{13}ClNOS$ (M$^+$+H): 242.0406. Found: 242.0408.

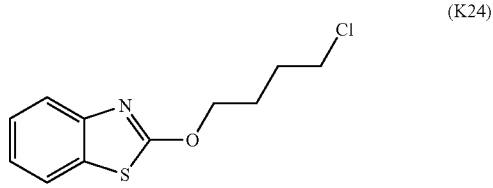 [SMILES: ClCCCCOc1nc2ccccc2s1]

(K24)

Example 18

Synthesis of 2-(4-Phenoxybutoxy)benzo[d]thiazole (K19)

Phenol (0.020 g, 0.21 mmol), NaOH (0.012 g, 0.31 mmol), and the compound K24 (0.05 g, 0.21 mmol) were reacted in the same manner as in Example 2 to afford the compound K19 (0.056 g, 90%).

Brown oil; $^1$H NMR (400 MHz, Acetone-$d_6$) δ 7.599 (d, J=7.9, 1H), 7.400~7.327 (m, 2H), 7.287~7.161 (m, 3H), 6.917 (d, 2H), 6.839~6.806 (m, 1H), 4.104 (t, 2H), 4.063 (t, J=6.2, 2H), 1.976~1.857 (m, 4H); HR-FABMS Calcd for $C_{17}H_{18}NO_2S$ (M$^+$+H): 300.1058. Found: 300.1061.

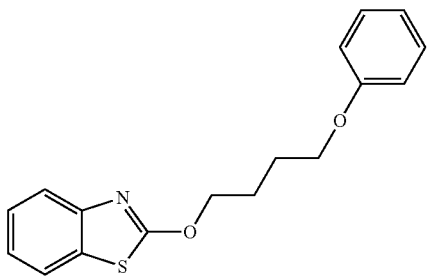

(K19)

Example 19

Synthesis of 4-(4-(Benzo[d]thiazol-2-yloxy)butoxy)benzonitrile (K20)

4-cyanophenol (0.025 g, 0.21 mmol), NaOH (0.012 g, 0.31 mmol), and the compound K24 (0.05 g, 0.21 mmol) were reacted in the same manner as in Example 2 to afford the compound K20 (0.059 g, 88%).

Transparent oil; $^1$H NMR (400 MHz, Acetone-$d_6$) δ 7.683 (d, J=9.2, 2H), 7.601 (d, J=7.8, 1H), 7.401~7.326 (m, 2H), 7.209 (t, J=7.7, 1H), 7.100 (d, J=9.2, 2H), 4.192 (t, J=6.0, 2H), 4.109 (t, J=6.8, 2H), 1.966~1.862 (m, 4H); HR-FABMS Calcd for $C_{18}H_{17}N_2O_2S$ (M$^+$+H): 325.1011. Found: 325.1015.

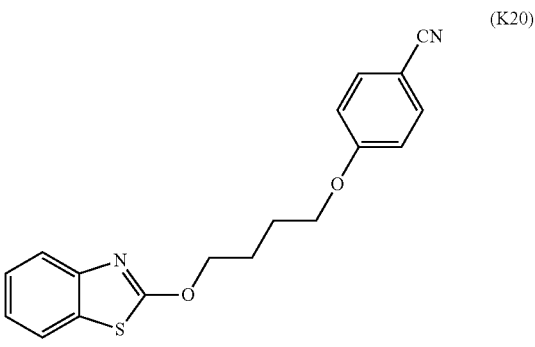 [SMILES: N#Cc1ccc(OCCCCOc2nc3ccccc3s2)cc1]

(K20)

Example 20

Synthesis of 4-(4-(Benzo[d]thiazol-2-yloxy)butoxy)-N-hydroxybenzamidine (K21)

The compound K20 (0.04 g, 0.12 mmol), triethylamine (0.025 g, 0.25 mmol), and NH$_2$OH.Cl (0.0172 g, 0.25 mmol) were reacted in the same manner as in Example 2 to afford the compound K21 as (0.018 g, 41%).

White powder, mp 170~171° C.; $^1$H NMR (400 MHz, Acetone-$d_6$) δ 8.699 (s, 1H), 7.634 (d, J=9.2, 2H), 7.600 (d, J=7.9, 1H), 7.401~7.331 (m, 2H), 7.206 (t, J=7.6, 1H), 6.913 (d, J=9.2, 2H), 5.370 (s, 2H), 4.123~4.082 (m, 4H), 1.948~1.871 (m, 4H); HR-FABMS Calcd for $C_{18}H_{20}N_3O_3S$ (M$^+$+H): 358.1225. Found: 358.1228.

(K21)

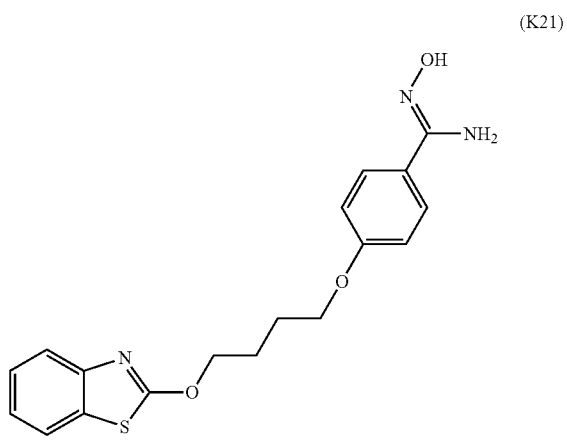 [SMILES: N/C(=N\O)c1ccc(OCCCCOc2nc3ccccc3s2)cc1]

Example 21

Synthesis of 4-(4-(Benzo[d]thiazol-2-yloxy)butoxy)-N,N-diisopropyl-3-methoxy Benzamide (K22)

The compound 10 (0.053 g, 0.21 mmol), NaOH (0.013 g, 0.32 mmol), and the compound K24 (0.051 g, 0.21 mmol) were reacted in the same manner as in Example 2 to afford the compound K22 (0.096 g, 99%).

Yellow oil; $^1$H NMR (400 MHz, Acetone-$d_6$) δ 7.599 (d, J=7.7, 1H), 7.387~7.349 (m, 2H), 7.227~7.174 (m, 1H), 6.959 (d, J=8.0, 1H), 6.894 (s, 1H), 6.832 (d, 1H), 4.148~4.090 (m, 4H), 3.813 (s, 3H), 3.746 (brs, 2H), 1.979~4.861 (m, 4H), 1.320 (brs, 12H); HR-FABMS Calcd for $C_{25}H_{33}N_2O_4S$ ($M^++H$): 457.2161. Found: 457.2158.

(K22)

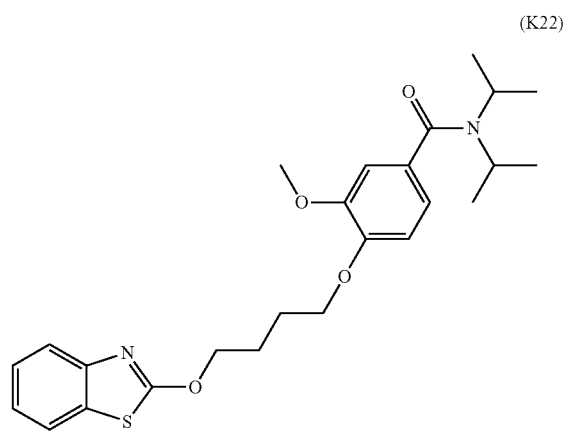 [SMILES: COc1cc(C(=O)N(C(C)C)C(C)C)ccc1OCCCCOc1nc2ccccc2s1]

Experimental Example 1

1) Culturing of Bone Marrow Cells

ICR mice (6~9 weeks old, male) were sacrificed by cervical dislocation, followed by immersion in 70% ethanol for sterilization. Dissection was made on the tibia skin to remove the muscle attached thereto. The tibia was excised by cutting the distal tibia and dislocating the patella. The tibia were then cut slightly at their opposite ends. A 25-gauge (G) syringe needle was inserted into the bone at one end and α-MEM (Minimum Essential Medium) was infused into the bone through the needle to collect bone marrow cells.

After centrifugation, a cell pellet was suspended in α-MEM and red blood cells in the suspension were removed with two volumes of Gey's solution. After centrifugation, the cell pellet was resuspended in α-MEM supplemented with 10% FBS.

2) Induction of Differentiation

After a primary culture of the bone marrow cells, the bone marrow cells were incubated overnight in 10 ng/ml M-CSF (macrophage colony-stimulating factor) and then for an additional three days in 30 ng/ml M-CSF. After Adhesive cells (BMM) were recovered, ng/ml RANKL and 30 ng/ml M-CSF or ng/ml RANKL, 30 ng/ml M-CSF in combination with various concentrations of the K11, K14, K17, K18, K19, or K22 compound were added to each well plated at a density of 1×10$^5$ cells/well and each well was incubated for 4 days. The incubated to cells were fixed for 10 min with 10% formalin and then re-fixed for 1 min with ethanol/acetone (1:1(v/v)). The cells were stained for TRAP (tartrate-resistant acid phosphatase). TRAP-positive cells having 3 or more nuclei were evaluated as multinucleated osteoclasts by observation under a microscope, and their IC$_{50}$ values are given in the following table 1.

| Compound | IC$_{50}$ (μM) |
|---|---|
| K11 | 1.56 |
| K14 | 7.77 |
| K17 | 23.35 |
| K18 | 18.40 |
| K19 | 17.68 |
| K22 | 2.20 |

3) Isolation and RT-PCR Analysis

Total RNA isolation was conducted using Easy-blue (Intron Biochemistry, Inc.). cDNA was synthesized from 1 mg of the total RNA using an oligodT primer and 10 mM dNTP, 1 unit of an RNase inhibitor and 4 units of Scrip reverse transcriptase (Fermentas, Life science) at 42° C. for 60 min, followed by termination by heating at 70° C. for 10 min. Polymerase chain reaction (PCR) conditions and primer sequences are given in the following table.

| | Primer Sequence | PCR Condition | Cycle |
|---|---|---|---|
| CTR | F: tttcaagaaccttagctgccagag<br>R: caaggcacggacaatgttgagaag | 94° C. 30 sec, 58° C. 30 sec, 72° C. 30 sec | 28 cycle |
| cath K | F: cttccaatacgtgcagcaga<br>R: acgcaccaatatcttgcacc | 94° C. 30 sec, 58° C. 30 sec, 72° C. 30 sec | 22 cycle |
| ATP6v0d2 | F: tcagatctcttcaaggctgtgctg<br>R: gtgccaaatgagttcagagtgatg | 94° C. 30 sec, 59° C. 30 sec, 72° C. 30 sec | 30 |

-continued

| Primer Sequence | | | PCR Condition | Cycle |
|---|---|---|---|---|
| DC-STAMP | F: | tggaagttcacttgaaactacgtg | 94° C. 30 sec, 58° C. 30 sec, 72° C. 30 sec | 30 |
|  | R: | ctcggtttcccgtcagcctctctc | | |
| αv-Integrin | F: | cctcagagagggagatgttcacac | 94° C. 30 sec, 60° C. 30 sec, 72° C. 30 sec | 28 |
|  | R: | aactgccaagatgatcacccacac | | |
| β3-Integrin | F: | gatgacatcgagcaggtgaaagag | 94° C. 30 sec, 55° C. 30 sec, 72° C. 30 sec | 32 |
|  | R: | ccggtcatgaatggtgatgagtag | | |
| β-actin | F: | tgtgatggtgggaatgggtcag | 94° C. 30 sec, 58° C. 30 sec, 72° C. 30 sec | 22 cycle |
|  | R: | tttgatgtcacgcacgatttcc | | |

4) Assay

The MTT (3-(4,5-dimethylthiazol-2-yl)-2,5-diphenyltetazolium bromide) assay was performed as described by Mosmann, with the addition of a modification. BMM cells were seeded at a density of $1\times10^4$ cells/well onto 96-well plates, treated with samples (K11, K14, K17, K18, K19, K22) and incubated for a predetermined period of time. The culture medium was to discarded and the cells were washed with PBS. The MTT solution (0.5 mg/ml) was then added in an amount of 100 μl/well to the plates, the plates were incubated for 5 hours with the plates wrapped in foil. Then, solubilization buffer (10% SDS in 0.01M HCl) was added in an amount of 100 μL/well to the plates and the plates were again wrapped in foil. After the plates were incubated for 16~17 hours, absorbance was measured at 570 nm.

Figure 2:
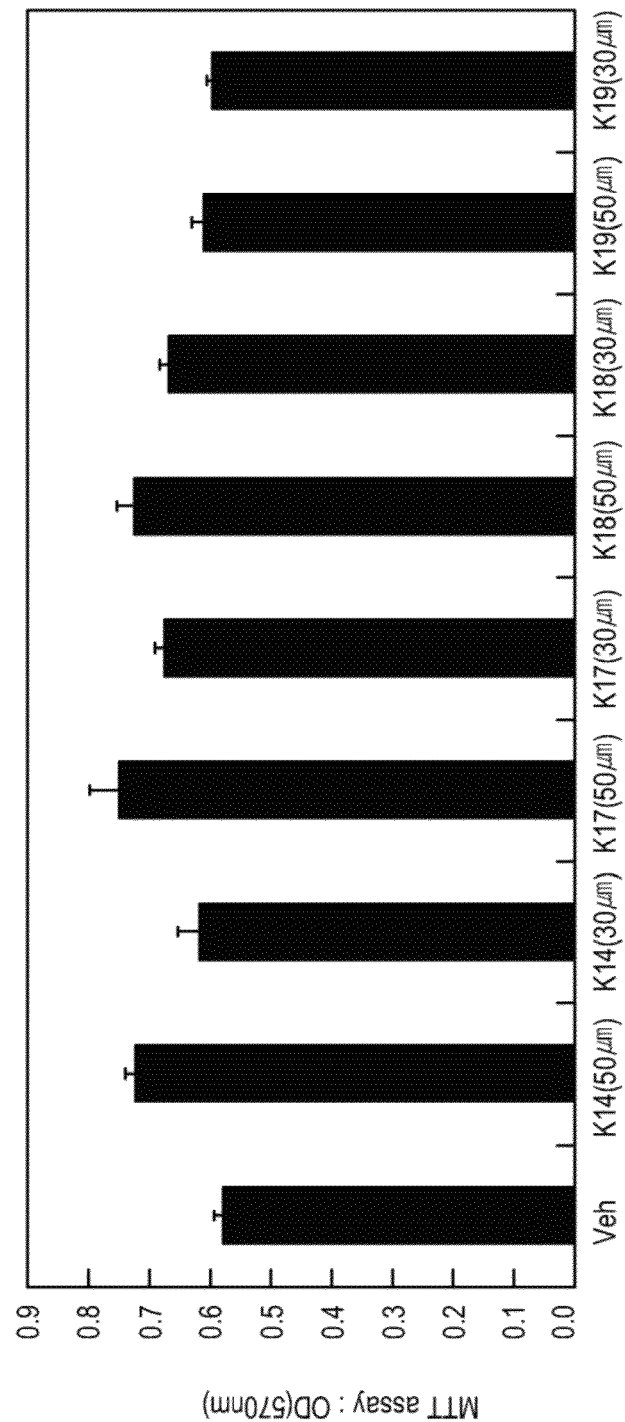

The inhibitory effect on osteoclast differentiation was found to be not attributed to the cell count difference due simply to chemical exposure by the MTT (3-(4,5-dimethylthiazol-2-yl)-2,5-diphenyltetazolium bromide) assay (FIGS. 1 and 2). Absorbance values read in the MTT assay results are in linear correlation with the number of cells. According to FIGS. 1 and 2, the absorbance values observed after treatment with the reagent were not reduced compared to the absorbance values observed prior to treatment with the reagent, indicating that the total count of cells was not decreased after treatment with the samples. Therefore, above experimental result was understood to come from the inhibitory activity of the samples against osteoclast differentiation, but not from cell death.

5) Pit Formation Assay

BMM cells were cultured for six days on dentine slices in 50 ng/ml RANKL and 30 ng/ml M-CSF, or 50 ng/ml RANKL 30 ng/ml and 10 μM K11 compound. After the cells on surfaces of dentine slice were washed, pits were stained with toluidin blue (J. T. Baker, UK, 1 μg/ml). Pits formed on the dentine slices by bone absorption were observed under a microscope and were analyzed.

Figure 3:
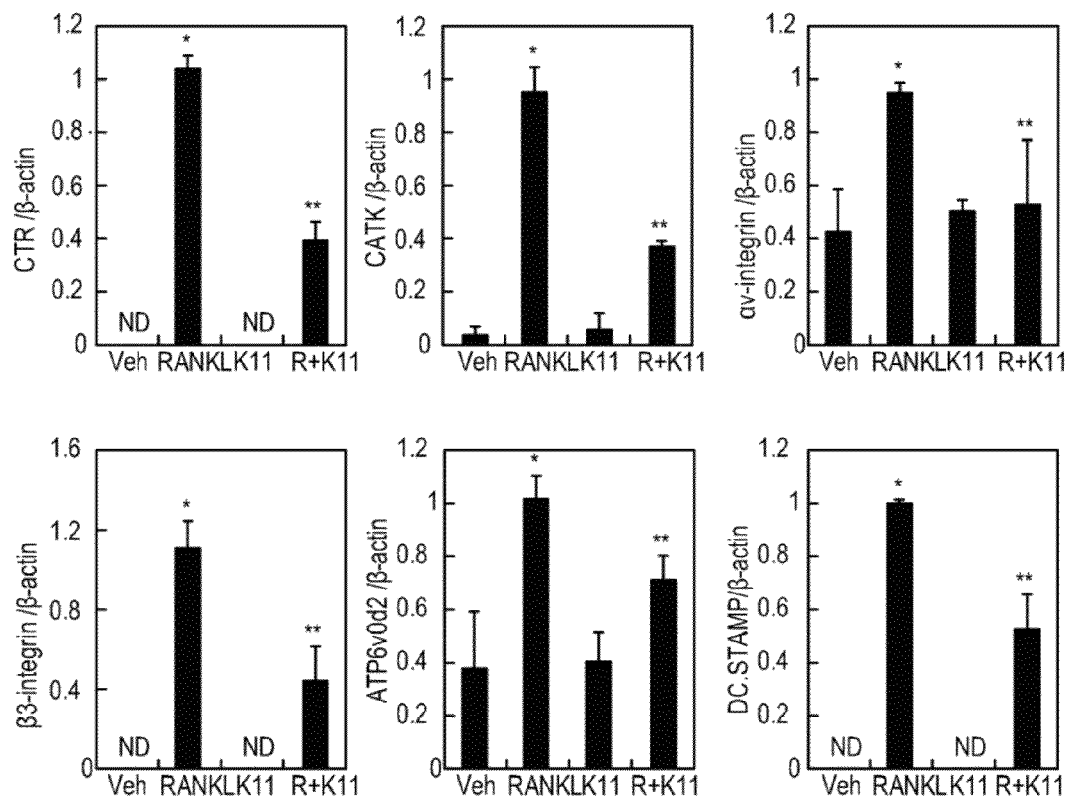
Figure 3:
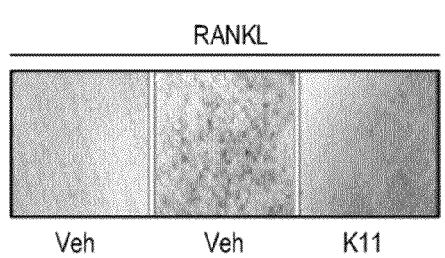
Figure 3:
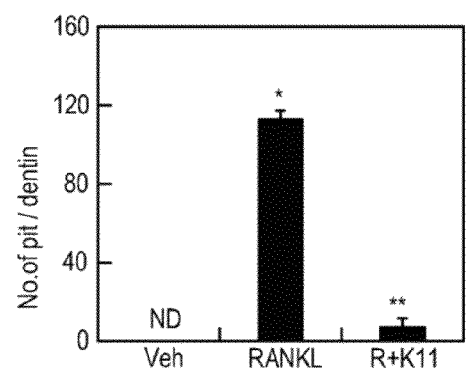

The results are shown in FIG. 3. In FIG. 3, Veh represents a control group treated with DMSO, RANKL represents a group treated with 50 ng/ml RANKL, K11 represents a group treated with 10 μM K11, R+K11 represents a group treated with 50 ng/ml RANKL following pretreatment with 10 μM K11 for 30 minutes, while * represents $p<0.05$ compared to Veh and ** represents *: $p<0.05$ compared to RANKL. N.D.=Not Detectable. FIG. 3A is graphs showing analyzed results of reverse transcription polymerase chain reaction (RT-PCR) performed for measurement of expression levels of osteoclast-specific marker genes (calcitonin receptor, cathepsin K, αv-integrin, β3-integrin, ATP6v0d2, DC-STAMP), FIG. 3B is a view of result of pits formed on dentine slices by bone absorption according to treatment with K11 compound and FIG. 3C is a graph showing analyzed results of the experiment results obtained in FIG. 3B. In FIG. 3A, the expression levels of osteoclast-specific marker genes were increased by treatment with RANKL, but were significantly decreased in the R+K11 group. In FIGS. 3B and 3C, a great number of pits were formed on dentine slices upon treatment with RANKL, but a significant reduction was found in the number of pits in the R+K11 group. This was coincident with the inhibitory activity of K11 compound against osteoclast differentiation, presuming that the K11 compound is inhibitory of osteoclast differentiation, thereby suppressing function of the bone resorption of osteoclasts.

6) Blot Analysis

After BMM cells treated with reagent were incubated for a predetermined period of time, the BMM cell were lysed in a lysis buffer and centrifuged. Following normalization to BSA (bovine serum albumin) standards, protein concentrations were quantitatively analyzed using a protein assay kit (Bio-Rad). Twenty micrograms of the protein was denatured and separated by SDS-PAGE (poly acrylamide gel electrophoresis) and transferred for 1 hour and 45 minutes onto a PVDF membrane in 80 V. Subsequently, the membrane was blocked with PBST (Phosphate Buffered Saline Tween-20) containing 5% skim milk, followed by reaction with anti-NFATc1 (Nuclear factor of activated T-cells cytoplasmic 1, 1:200, Santa Cruz) antibody or anti-c-fos (1:1000, Cell Signaling) antibody as a primary antibody, respectively (1:200 ratio herein indicated means dilution of 200 times). After the membrane was washed five times with TBST and reacted with HRP (horseradish peroxidase)-conjugated secondary antibody, the protein was visualized using ECL Advance (Amersham Co.) and analyzed.

Figure 4:
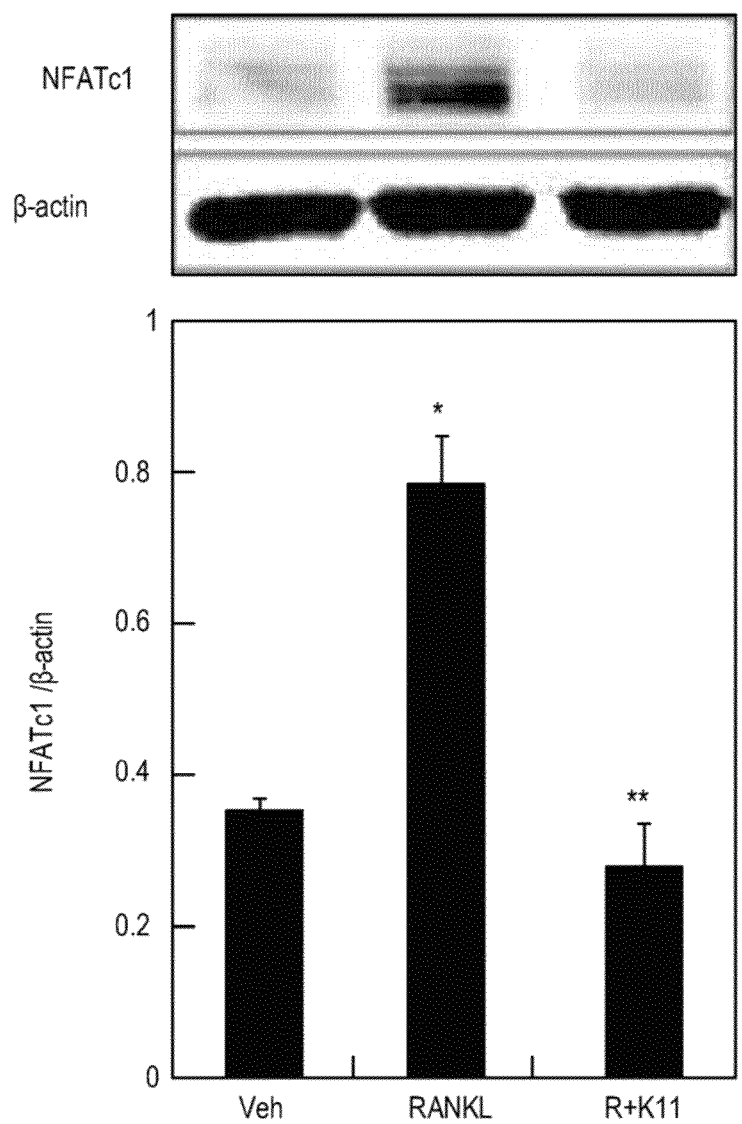
Figure 5:
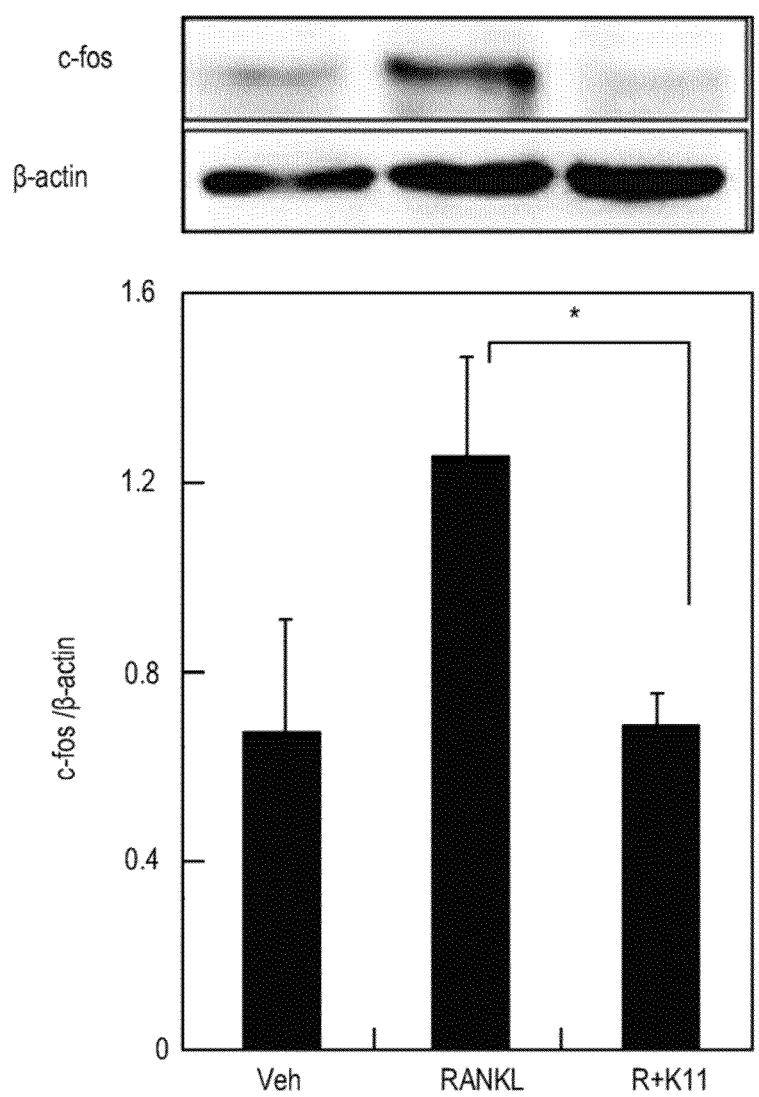

The results are shown in FIGS. 4 and 5. In FIGS. 4 and 5, veh represents a control group treated with DMSO, RANKL represents a group treated with 200 ng/ml RANKL, R+K11 represents a group treated with 200 ng/ml RANKL following pretreatment with 10 μM K11 for 30 minutes, while * represents $p<0.05$ compared to Veh and ** represents *: $p<0.05$ compared to RANKL.

In FIGS. 4 and 5, an increase in the expression level of NFATc1 and c-fos, which is typically accompanied by osteoclast differentiation, was observed in the RANKL group while the effect of RANKL was reduced in the R+K11 group, indicating that the K11 compound blocks RANKL-induced osteoclast differentiation signaling.

7) Statistical Treatment

Experimental result is presented as means±standard deviation. The difference between the two groups was determined by Student's t-test and was considered statistically significant when $P<0.05$.

The foregoing is for the purpose of illustration only, and it is not intended to limit the present invention. Although the present invention have been described with reference to the accompanying example embodiments of the present invention, it is understood that various changes and modifications can be made by one ordinary skilled in the art within the spirit and scope of the present invention which is defined by the following claims. Thus, the changes and modifications are included within the scope of the present invention which is defined by the following claims, the present invention include the following claims and equivalents of the claims.

What is claimed is:

1. A compound or pharmaceutically acceptable salt thereof selected from the group consisting of:
   4-(5-(benzo[d]thiazol-2-yloxy)pentyloxy)-N,N-diisopropyl-3-methoxybenzamide,
   2-(5-(3-chlorophenoxy)pentyloxy)benzo[d]thiazole,
   2-(5-(2-methoxyphenoxy)pentyloxy)benzo[d]thiazole,
   2-(5-(2-fluorophenoxy)pentyloxy)benzo[d]thiazole,
   2-(4-phenoxybutoxy)benzo[d]thiazole, and
   4-(4-(benzo[d]thiazol-2-yloxy)butoxy)-N,N-diisopropyl-3-methoxybenzamide.

2. The compound or pharmaceutically acceptable salt thereof of claim 1, being selected from the group consisting of:
   4-(5-(benzo[d]thiazol-2-yloxy)pentyloxy)-N,N-diisopropyl-3-methoxybenzamide, and
   4-(4-(benzo[d]thiazol-2-yloxy)butoxy)-N,N-diisopropyl-3-methoxybenzamide.

3. A method for preparing a compound represented by the following Chemical Formula I or pharmaceutically acceptable salts thereof:
   a) reacting 2-hydroxybenzothiazole with 1-bromo-5-chloropentane or 1-bromo-4-chlorobutane in presence of a base to give a compound represented by the following Chemical Formula II; and
   b) reacting the compound of Chemical Formula II with a compound represented by the following Chemical Formula III in presence of a base to synthesize the compound of Chemical Formula I:

[Chemical Formula II]

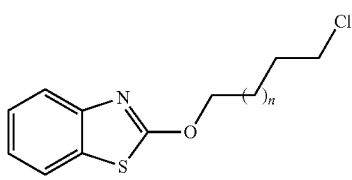

[Chemical Formula III]

H—R$_1$

[Chemical Formula I]

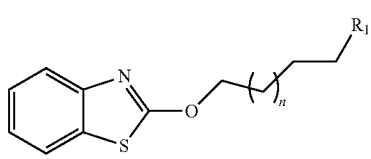

wherein,
n is 1 or 2, and
R$_1$ is

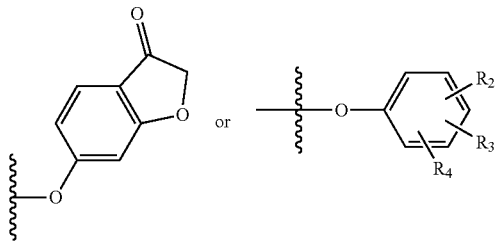

wherein R$_2$, R$_3$ and R$_4$ are independently bonded to at least one of the carbon atoms of the phenyl ring at ortho-, meta- or para-position to the carbon atom to which the oxygen atom is attached, and is independently a hydrogen atom, fluoro, chloro, bromo, iodo, cyano, nitro, C1-4 alkyl, C1-4 alkoxy, C2-4 alkenyl, triazole, piperidine, pyridine or

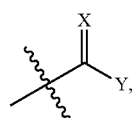

wherein X is —NOH, —NH.HCl, O or S and Y is —NR$_5$R$_6$ or —OR$_7$, wherein R$_5$, R$_6$ and R$_7$ are independently an hydrogen atom or C1-4 alkyl.

4. The method of claim 3, wherein the base used in step a) is selected from the group consisting of potassium carbonate, sodium carbonate, calcium carbonate and sodium phosphate.

5. The method of claim 3, wherein the base used in step b) is selected from the group consisting of sodium hydroxide, potassium carbonate, potassium carbonate, and sodium phosphate.

6. The method of claim 3, where steps a) and b) are conducted at a reaction temperature of from about 50° C. to about 90° C.

7. A composition comprising a compound or pharmaceutically acceptable salt thereof selected from the group consisting of:
   4-(5-(benzo[d]thiazol-2-yloxy)pentyloxy)-N,N-diisopropyl-3-methoxybenzamide,
   2-(5-(3-chlorophenoxy)pentyloxy)benzo[d]thiazole,
   2-(5-(2-methoxyphenoxy)pentyloxy)benzo[d]thiazole,
   2-(5-(2-fluorophenoxy)pentyloxy)benzo[d]thiazole,
   2-(4-phenoxybutoxy)benzo[d]thiazole, and
   4-(4-(benzo[d]thiazol-2-yloxy)butoxy)-N,N-diisopropyl-3-methoxybenzamide.

8. The composition of claim 7, wherein the compound or pharmaceutically acceptable salt, thereof is selected from the group consisting of 4-(5-(benzo[d]thiazol-2-yloxy)pentyloxy)-N,N-diisopropyl-3-methoxybenzamide and 4-(4-(benzo[d]thiazol-2-yloxy)butoxy)-N,N-diisopropyl-3-methoxybenzamide.

9. The composition of claim 7, further comprising a pharmaceutically acceptable carrier.

10. A method for alleviating, preventing or treating osteoporosis, comprising administering a compound represented by the following Chemical Formula I or the pharmaceutically acceptable salt thereof to a subject:

[Chemical Formula I]

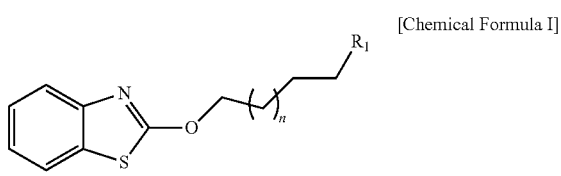

wherein,
n is 1 or 2,
R₁ is fluoro, chloro, bromo, iodo,

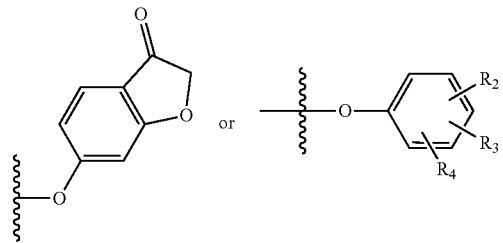

wherein R₂, R₃ and R₄ are independently bonded to at least one of the carbon atoms of the phenyl ring at ortho-, meta- or para-position to the carbon atom to which the oxygen atom is attached, and is independently a hydrogen atom, fluoro, chloro, bromo, iodo, cyano, nitro, C1-4 alkyl, C1-4 alkoxy, C2-4 alkenyl, triazole, piperidine, pyridine or

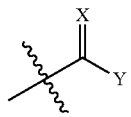

wherein X is —NOH, —NH.HCl, O or S and Y is —NR₅R₆ or —OR₇ wherein R₅, R₆ and R₇ are independently a hydrogen atom or C1-4 alkyl.

11. The method of claim 10, wherein
n is 1 or 2, and
R₁ is fluoro, chloro, bromo,

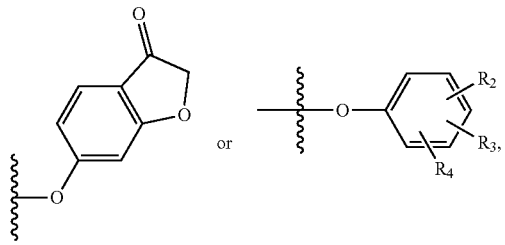

wherein R₂, R₃ and R₄ are independently bonded to at least one of the carbon atoms of the phenyl ring at ortho-, meta- or para-position to the carbon atom to which the oxygen atom is attached, and is independently a hydrogen atom, fluoro, chloro, bromo, iodo, cyano, C1-4 alkyl, C1-4 alkoxy, triazole, or

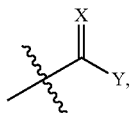

wherein X is —NOH, —NH.HCl or O and Y is —NR₅R₆ or —OR₇, wherein R₅, R₆ and R₇ are independently an hydrogen atom or C1-4 alkyl.

12. The method of claim 11, wherein the compound represented by Chemical Formula I or the pharmaceutically acceptable salt thereof is selected from the group consisting of:

2-(5-chloropentyloxy)benzo[d]thiazole,
2-(5-phenoxypentyloxy)benzo[d]thiazole,
4-(5-(benzo[d]thiazol-2-yloxy)pentyloxy)benzonitrile,
4-(5-(benzo[d]thiazol-2-yloxy)pentyloxy)-N-hydroxybenzamidine,
4-(5-(benzo[d]thiazol-2-yloxy)pentyloxy)benzamidine HCl,
methyl 4-(5-(benzo[d]thiazol-2-yloxy)pentyloxy)-3-methoxybenzoate,
4-(5-(benzo[d]thiazol-2-yloxy)pentyloxy)-3-methoxybenzoic acid,
4-(5-(benzo[d]thiazol-2-yloxy)pentyloxy)-N,N-diisopropyl-3-methoxy benzamide,
4-(5-(benzo[d]thiazol-2-yloxy)pentyloxy)-N,N-diethyl-3-methoxybenzamide,
2-(5-(3,5-dimethylphenoxy)pentyloxy)benzo[d]thiazole,
2-(5-(4-(1H-1,2,4-thiazol-1-yl)phenoxy)pentyloxy)benzo[d]thiazole,
2-(5-(4-fluorophenoxy)pentyloxy)benzo[d]thiazole,
2-(5-(3-chlorophenoxy)pentyloxy)benzo[d]thiazole,
6-(5-(benzo[d]thiazol-2-yloxy)pentyloxy)benzofuran-3(2H)-one,
2-(5-(2-methoxyphenoxy)pentyloxy)benzo[d]thiazole,
2-(5-(2-fluorophenoxy)pentyloxy)benzo[d]thiazole,
2-(4-chlorobutoxy)benzo[d]thiazole,
2-(4-phenoxybutoxy)benzo[d]thiazole,
4-(4-(benzo[d]thiazol-2-yloxy)butoxy)benzonitrile,
4-(4-(benzo[d]thiazol-2-yloxy)butoxy)-N-hydroxybenzamidine, and
4-(4-(benzo[d]thiazol-2-yloxy)butoxy)-N,N-diisopropyl-3-methoxybenzamide.

* * * * *

UNITED STATES PATENT AND TRADEMARK OFFICE
CERTIFICATE OF CORRECTION

PATENT NO. : 8,604,214 B2  Page 1 of 1
APPLICATION NO. : 13/523612
DATED : December 10, 2013
INVENTOR(S) : Hea-Young Parkchoo et al.

It is certified that error appears in the above-identified patent and that said Letters Patent is hereby corrected as shown below:

In the Claims

Column 32, Line 57, Claim 8:
"pharmaceutically acceptable salt, thereof is selected from the" should read, --pharmaceutically acceptable salt thereof is selected from the--.

Signed and Sealed this
Seventh Day of October, 2014

Michelle K. Lee
*Deputy Director of the United States Patent and Trademark Office*